US006428999B1

(12) United States Patent
Ito et al.

(10) Patent No.: US 6,428,999 B1
(45) Date of Patent: Aug. 6, 2002

(54) SPHINGOLIPID CERAMIDE N-DEACYLASE, METHODS FOR PRODUCING SPHINGOLIPIDS AND SPHINGOLIPID DERIVATIVES, AND SPINGOLIPID CERAMIDE N-DEACYLASE GENE

(75) Inventors: Makoto Ito, Fukuoka; Toyohisa Kurita, Shiga; Katsuhiro Kita, Nagasaki; Noriyuki Sueyoshi; Susumu Mitsutake, both of Fukuoka; Masanori Fujita, Aichi; Nozomu Okino, Fukuoka; Hiroyuki Izu; Ikunoshin Kato, both of Shiga, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/160,036

(22) Filed: Sep. 25, 1998

Related U.S. Application Data

(63) Continuation-in-part of application No. 08/881,468, filed on Jun. 24, 1997, now abandoned, which is a continuation-in-part of application No. 08/504,678, filed on Jul. 20, 1995, now abandoned, and a continuation-in-part of application No. PCT/JP97/02483, filed on Jul. 17, 1997.

(30) Foreign Application Priority Data

| Jul. 21, 1994 | (JP) | 6-190133 |
| Jul. 19, 1996 | (JP) | 8-207606 |
| Jul. 26, 1996 | (JP) | 8-214065 |
| Mar. 26, 1998 | (JP) | 10-096989 |

(51) Int. Cl.⁷ .............. C12N 9/80; C12N 1/20
(52) U.S. Cl. ............ 435/228; 435/252.1; 435/253.3; 435/227
(58) Field of Search .............. 435/227, 228, 435/253.3, 252.1

(56) References Cited

U.S. PATENT DOCUMENTS 5,143,841 A 9/1992 Hirabayashi et al. ....... 435/227

FOREIGN PATENT DOCUMENTS

| EP | A373038 | 6/1990 | |
| EP | WO 94/26919 | 11/1994 | C12P/13/02 |
| EP | 0 707 063 A1 | 4/1996 | C12N/9/80 |
| JP | 06078782 | 3/1994 | |
| JP | 07107988 | 4/1995 | |
| JP | 7508889 | 10/1995 | |
| JP | 884587 | 4/1996 | |
| WO | WO 8911295 | 11/1989 | |

OTHER PUBLICATIONS

M. Ito et al. "A Novel Enzyme That Cleaves the N–Acyl Linkage of Ceramides in Various Glycoshingolipids as Well as Sphingomyelin to Produce Their Lyso Forms" J. Biol. Chem. 270(41): 24370–24374, Oct. 1995.*

Y. Hirabayashi et al., "A Novel Glycoshingolipid Hydrolyzing Enzyme, Glycosphingolipid Ceramide Deacylase, Which Cleaves the Linkage Between the Fatty Acid and Sphingosine Base in Glycosphingolipids" J. Biochem. 103: 1–4, Oct. 1995.*

Hirabayashi et al., "A Novel Glycosphingolipd Hydrolyzing Enzyme, Glycosphingolipid Ceramide Deacylase, Which Cleaves the Linkage between the Fatty Acid an Sphingosine Base in Glycosphingolipids" *The Journal of Biochemistry*, vol. 103, No. 1, Jan. 1998, Tokyo, pp. 1–4.

Makoto Ito et al., "A Novel Enzyme That Cleaves the N–Acyl Linkage of Ceramids in Various Glycosphingolipids as Well as Sphingomyelin to Produce Their Lyso Forms" *The Journal of Biochemistry*, vol. 270, No. 41, Oct. 13, 1995, U.S.A., pp. 24370–24374.

Office Action from related Chinese Patent Application with English language translation.

K. Drautz and H. Waldman, Enzyme Catalysts in Organic Synthesis, VCH Weinheim, 96–98 (1995) XP–002151209.

S. Mitsutake et al., [¹⁴C] Ceramide Synthesis by Sphingolipid Ceramide N–Deacylase: New Assay for Ceramidae Activity Detection, Anal. Biochem. 247:52–57 (1997).

* cited by examiner

*Primary Examiner*—Rebecca E. Prouty
(74) *Attorney, Agent, or Firm*—Sughrue Mion, PLLC

(57) ABSTRACT

The present invention relates to a novel sphingolipid ceramide N-deacylase (SCDase) having a wide substrate specificity; a method for enzymatically producing a lysosphingolipid or a sphingolipid derivative using the SCDase which is useful in the fields of medicine, carbohydrate engineering, cell engineering, and the like; the lysosphingolipid or sphingolipid derivative obtained by this production method; a gene which encodes a polypeptide having an SCDase activity useful in sphingolipid technology; a method for industrially producing a polypeptide having an SCDase deacylase activity and a recombinant polypeptide thereof using a transformant to which the gene is introduced; a probe or primer which hybridizes to the gene; and an antibody or a fragment thereof which specifically binds to the polypeptide.

12 Claims, 11 Drawing Sheets

SPHINGOLIPID CERAMIDE N-DEACYLASE, METHODS FOR PRODUCING SPHINGOLIPIDS AND SPHINGOLIPID DERIVATIVES, AND SPINGOLIPID CERAMIDE N-DEACYLASE GENE

CROSS-REFERENCE TO RELATED APPLICATION

This application is a continuation-in-part application of U.S. application Ser. No. 08/881,468, filed on Jun. 24, 1997; now abandoned, which is a continuation-in-part of Ser. No. 08/504,678, filed Jul. 20, 1995, now abandoned and a continuation in part of PCT/JP97/02483 filed on Jul. 17, 1997.

BACKGROUND OF THE INVENTION

1. Technical Field

The present invention relates to a novel sphingolipid ceramide N-deacylase (hereinafter often referred to as "SCDase") having a wide substrate specificity. Furthermore, the present invention relates to methods for enzymatically producing lysosphingolipid or sphingolipid derivatives using the SCDase which is useful in the fields of medicine, carbohydrate engineering, cell engineering, and the like, and the lysosphingolipid or sphingolipid derivatives obtained by such a production method. Moreover, the present invention relates to a gene which encodes a polypeptide having an SCDase activity useful in sphingolipid technology. Also, the present invention relates to a method for industrially producing a polypeptide having an SCDase activity and a recombinant polypeptide thereof using a transformant to which the gene is introduced, a probe or primer which hybridizes to the gene, and an antibody or a fragment thereof which specifically binds to the polypeptide.

2. Description of the Background Art

In recent years, attention has been paid to various physiological functions of a sphingolipid as well as a glycerolipid as components constituting the cell membrane lipid of eucaryotes. An SCDase which acts on the sphingolipid to form a fatty acid and a lysosphingolipid is not only useful for the elucidation of the physiological actions of the lyso-form sphingolipid but also considerably important in the field of sphingolipid technology such as preparation of sphingolipid derivatives and labeling of a sphingolipid.

"Sphingolipid" is a generic name for lipids having a long-chain base sphingoid such as glycosphingolipids, sphingophospholipids (involving sphingophosphonolipids) and ceramides. Sphingolipids, which have a ceramide having a long-chain fatty acid with a nonuniform chain length bonded via an acid-amide bond to the amino group of the sphingoid as the common structure, are widely distributed in lower animals to higher animals. Recently, it has been clarified that these sphingolipids participate in important roles in biological activities of cell proliferation, induction of differentiation, apoptosis and the like. Also, attempts have been made to employ these sphingolipids in cosmetics and the like since they are constituents of the cell surface layer.

On the other hand, N-deacylated sphingolipids, in which the fatty acid bonded via an acid-amide bond to the amino group of the sphingoid in the sphingolipid has been eliminated, are called lysosphingolipids. It has been clarified that these lysosphingolipids have biological activities similar to those of the sphingolipids.

Moreover, when re-acylated lysosphingolipids having a free amino group in the sphingoid moiety are useful as starting materials for synthesizing lysosphingolipid derivatives (sphingolipid derivatives). For example, sphingolipids having a uniform fatty acid composition or those differing in the fatty acid chain length from the starting ones can be re-synthesized thereby. It is also possible to obtain sphingolipids labeled with chromophores, radioisotopes such as $^{14}C$ and the like. Furthermore, lysosphingolipids can be immobilized onto a carrier using the free amino group thereof.

In general, naturally occurring glycolipids such as glycosphingolipids show wide molecular variety depending on a fatty acid moiety even if they have the same carbohydrate chain. For example, Forssman glycolipid (Gb5Cer) derived from a horse kidney includes at least ten different molecular species depending on its fatty acid moiety. Recently, it has revealed that the existing form or antigenicity of glycolipids in a lipid bilayer are greatly influenced by their fatty acid molecular species. Thus, attention has been paid to the structure of a fatty acid in view of the physiological function of a glycolipid. It has been further found that the substrate specificity of enzymes relating to the degradation and synthesis of sphingolipids (including glycolipids and sphingomyelin) depends on fatty acid molecular species.

In order to elucidate the above subject, it has been required to develop technique for simply and easily converting naturally occurring sphingolipids including heterologous fatty acid molecular species into glycolipids having a single fatty acid species. It has also been desired to prepare a fluorescence-labeled sphingolipid by substituting a fatty acid of a sphingolipid with a fluorescent substance since such a fluorescence-labeled sphingolipid is expected to be not only a reagent important for contributing to the elucidation of intracellular metabolism or a transport route of sphingolipids but also a highly sensitive substrate for enzymes synthesizing or degrading a sphingolipid.

Known methods for producing lysosphingolipids include chemical methods, enzymatic methods and microbial methods.

The chemical methods include hydrazinolysis and alkaline hydrolysis in an alcohol solvent. When a glycosphingolipid containing sialic acid (i.e., ganglioside) is treated by these methods, the deacylation of the sialic acid moiety also proceeds at the same time. In the case of a glycosphingolipid containing aminosugar, the N-acetyl group is liberated and thus a de-N-acetyl lysoglycolipid is formed. It is therefore necessary that, after the completion of the deacylation, a protecting group is selectively introduced into the amino group in the lipid moiety and the sialic acid moiety is re-acylated followed by deprotection. Various by-products are formed by these procedures. That is to say, the production of lysoglycolipids by these chemical methods require great labor and technical skill. In addition, it is very difficult to prepare a lyso-form of a polysialoganglioside having plural sialic acids, such as GQ1b, in accordance with the conventional chemical methods.

On the other hand, there have been known chemical methods for obtaining the lyso-form of a sphingomyelin which is a sphingophospholipid. A generally known example of the chemical methods is one comprising hydrolysis with hydrochloric acid in an alcohol solvent. According to this method, however, not only natural a D-erythro (2S,3R) stereoisomer but also an L-threo (2S,3S) stereoisomer are formed, which reduces the yield of the final product and it is very difficult to separate these isomers from each other. When sphingomyelin is treated by the known methods, a choline phosphate group might be possibly liberated, which reduces the yield of the final product.

On the other hand, there have been known methods wherein enzymes forming lyso-forms from glycosphingolipids are employed. However, the method using a ganglioside ceramidase produced by an actinomycetes of the genus Nocardia fails to provide any neutral glycolipid of the lyso-form due to the substrate specificity of the enzyme (JP-A-64-60379 (the term "JP-A" as used herein means an unexamined published Japanese patent application). The method using an enzyme produced by an actinomycetes of the genus Rhodococcus or processed cells thereof fails to provide the lyso-form of any acidic glycolipid (ganglioside) (JP-A-6-78782).

An enzyme capable of hydrolyzing a bond between a sphingosine base and a fatty acid of a ceramide, which is called ceramidase (EC 3.5.1.23) [*Journal of Biological Chemistry,* 241:3731–3737 (1966); *Biochemistry,* 8:1692–1698 (1969); *Biochemica et Biophysica Acta,* 176:339–347 (1969); and *Science,* 178:1100–1102 (1972)], cannot hydrolyze a bond between a sphingosine base and a fatty acid in the ceramide moiety of a glycolipid. Namely, none of known enzymes can widely act on sphingolipids involving glycosphingolipids (ganglioside, neutral glycolipids) and sphingomyelins.

With regard to use of a microorganism or its extract, an actinomycetes of the genus Streptomyces capable of producing a glycosphingolipid ceramide deacylase is employed in a method described in JP-A-7-107988. In this method, a glycosphingolipid is added to the medium and converted into the lyso-form therein. However, this method is also poor in efficiency. Owing to the substrate specificity, moreover, the enzyme cannot act on ganglioside GM3 and neutral glycolipids (i.e., lactosyl ceramide, glycosyl ceramide and galactosyl ceramide). Thus it is impossible to obtain the lyso-forms of these glycolipids by this method.

As discussed above, the conventional chemical, enzymatic and microbial methods for producing lysosphingolipids suffer from such troubles that undesired by-products are formed, great labor and technical skill are required, or the substrate is restricted. Furthermore, these methods can achieve only poor efficiency.

As a common structure, sphingolipids have a ceramide structure in which a long-chain fatty acid having a nonuniform chain length bonded to the amino group of the sphingoid via an acid-amide bond. With regard to the method for producing sphingolipids or sphingolipid derivatives by modifying or substituting the long-chain fatty acid of sphingolipids, methods are known in which they are synthesized chemically or enzymatically using a lysosphingolipid as the starting material which lacks the fatty acid bonded by the acid-amide bond to the amino group of the sphingoid in the sphingolipid.

As the chemical method, there are methods in which a fatty acid or a fatty acid derivative is condensed to the lyso-form amino group by the following techniques. For example, known are a method in which a fatty acid active ester (for example, N-hydroxysuccinimide ester of a fatty acid) is used, a method in which a fatty acid and a coupling agent (for example, carbonyldiimidazole, dicyclohexylcarbodiimide or the like) are used, a method in which a fatty acid anhydride is used, a method in which a fatty acid chloride is used, and the like.

Methods in which a lysoganglioside is used as the lyso-form of an acidic glycolipid are reported in *Methods in Enzymology,* 138:319–341 (1987), European Patent 373039 B1 (1994) and European Patent 765883 A1 (1997). Also, a method in which a sphingosyl-phosphorylcholine (lysosphingomyelin) is used as the lyso-form of sphingo-phospholipid is described in *Journal of Lipid Research,* 28:710–718 (1987).

According to these methods, side reactions (for example, O-acylation and the like) occur in some cases, so that it is necessary to employ complex steps for use of protecting groups, purification and the like, in order to obtain an N-acylated product selectively. Also, when it is required to acylate only the amino group of the sphingoid in a sphingolipid selectively which has an amino group other than the amino group of the sphingoid, such as de-N-acetyllysoganglioside which is obtained by chemically deacylating a ceramide ciliatine which is one of sphingo-phosphonolipids or a glycosphingolipid containing aminosugar, complex steps, such as a step of introduction of protecting groups, partial acylation, partial deacylation after the acylation, and a step of selective N-acylation after incorporation of de-N-acetyllysoganglioside into liposomes, are required, and therefore it is difficult to conduct the selective acylation.

On the other hand, an enzymatic synthesis method is described in International Publication No. WO 94/26919. In this method, a condensation reaction is carried out by lipase in an organic solvent, so that a substantially water-free organic solvent is required and the substrate is limited depending on its solubility. International Publication No. WO 94/26919 discloses an enzymatic synthesis method of a ceramide and a hybrid ceramide, but the reaction is not specific so that the formation of O-acylated products is found. Furthermore, when the substrate has a plurality of amino groups similar to the case of the chemical synthesis methods, it is difficult to carry out the specific reaction with only the amino group of the sphingoid.

As described above, in the previous method for synthesizing sphingolipids or sphingolipid derivatives by chemically or enzymatically modifying or substituting the long-chain fatty acid in the sphingolipid, undesirable by-products are formed, and the substrate is limited. Additionally, in the previous methods, the lysosphingolipid which lacks a fatty acid bonded by an acid-amide bond to the 2-position of the sphingoid in the sphingolipid is used as the starting material. Therefore, when intended sphingolipids or sphingolipid derivatives are synthesized, it is required to prepare a lysosphingolipid prior to the synthesis.

Furthermore, when the above-described SCDase useful in the field of sphingolipid technology is produced from an enzyme producing organism industrially advantageously, the amount of the naturally existing enzyme is small or, in order to induce the production of the enzyme, it is necessary to culture the enzyme producing organism by adding a ganglioside mixture to the medium, so that free fatty acids are formed in the culture medium and enzymes other than the SCDase, such as a sphingomyelinase and the like, are simultaneously produced, thus causing a difficulty in separating and purifying the SCDase of interest from these free fatty acids and the enzymes contaminated.

Consequently, great concern has been directed toward the development of a method by which this enzyme can be produced with a more lower cost and higher purity.

Although there are reports on the purification of the SCDase from various enzyme producing organisms as described above, there are no reports on the amino acid sequence and the structure of the SCDase, so that the amino acid sequence and gene structure are entirely unclear and therefore, it is difficult to produce an SCDase by means of genetic engineering techniques.

SUMMARY OF THE INVENTION

An object of the present invention is to provide an SCDase having a wider substrate specificity than those of the conventionally known glycolipid ceramide deacylases.

Furthermore, an object of the present invention is to provide a method for enzymatically producing a lysosphingolipid, which is useful in the field of sphingolipid engineering, using the above SCDase in an industrial scale without producing by-products.

Moreover, an object of the present invention is to provide a microorganism capable of producing an SCDase for use in the above-described method.

Still furthermore, an object of the present invention is to provide lysosphingolipids and lysosphingolipid derivatives obtained by the above-described method.

Still moreover, an object of the present invention is to provide a production method for specifically synthesizing sphingolipids or sphingolipid derivatives having a modified or substituted long-chain fatty acid bonded to the sphingoid from not only a lysosphingolipid but also a sphingolipid.

Also, an object of the present invention is to provide sphingolipids or sphingolipid derivatives obtained by the production method.

Additionally, an object of the present invention is to provide a gene which encodes a polypeptide having an SCDase activity; a method for industrially producing a polypeptide having an SCDase activity using a transformant introduced to the gene, and such a recombinant peptide; a probe or primer which hybridizes to the gene; and an antibody or a fragment thereof which specifically binds to the polypeptide.

The present invention mainly relates to the following 1) to 19):

1) an SCDase having physicochemical properties of:
   (i) acting on a ceramide moiety in the molecule of a sphingolipid and forming a lysosphingolipid and a fatty acid;
   (ii) acting on neutral glycosphingolipids, acidic glycosphingolipids, sphingomyelins and ceramides;
   (iii) having an optimum pH value range of from 5 to 8.5; and
   (iv) having an optimum temperature of about 40° C.;

2) a method for producing an SCDase which comprises:
   culturing a strain belonging to the genus Pseudomonas or Shewanella capable of producing an SCDase to produce an SCDase; and
   recovering the SCDase from the culture;

3) a method for producing a lysosphingolipid which comprises:
(A) treating a sphingolipid with the above SCDase to obtain a reaction mixture; and
   recovering a lysosphingolipid from the reaction mixture, or
(B) a method for producing a lysosphingolipid which comprises:
   subjecting a sphingolipid to a contact reaction with a microorganism capable of producing an SCDase to obtain a reaction mixture; and
   recovering a lysosphingolipid from the reaction mixture;

4) a lysosphingolipid which is obtained by the above method 3);

5) a method for producing a lysosphingolipid derivative which comprises subjecting the lysosphingolipid of above 4) to a substitution reaction;

6) a lysosphingolipid derivative which is obtained by the above method 5);

7) a method for producing a sphingolipid or a sphingolipid derivative, which comprises enzymatically reacting a sphingolipid with an aliphatic carboxylic acid having or free of a marker using an enzyme which can specifically hydrolyze an acid-amide bond between a sphingoid and a fatty acid in a sphingolipid to obtain another sphingolipid or sphingolipid derivative having a different fatty acid chain;

8) a method for producing a sphingolipid or a sphingolipid derivative, which comprises enzymatically reacting a lysosphingolipid with an aliphatic carboxylic acid having or free of a marker using an enzyme which can specifically hydrolyze an acid-amide bond between a sphingoid and a fatty acid in a sphingolipid to obtain a sphingolipid or sphingolipid derivative;

9) a method for producing a sphingolipid or a sphingolipid derivative, which comprises enzymatically reacting at least two different sphingolipids using an enzyme which can specifically hydrolyze an acid-amide bond between a sphingoid and a fatty acid in a sphingolipid to obtain other sphingolipid or sphingolipid derivative having an exchanged fatty acid chain;

10) the method for producing a sphingolipid or a sphingolipid derivative, which comprises using a microorganism which is capable of producing the enzyme, instead of the enzyme in the above 7) to 9);

11) a sphingolipid or sphingolipid derivative, which is obtained by any one of the above methods 7) to 10);

12) a bacterium belonging to the genus Pseudomonas or Shewanella which is capable of producing an SCDase, or a mutant thereof;

13) an isolated gene which encodes a polypeptide having an SCDase activity.

14) a recombinant vector which comprises the gene of the above 13);

15) a transformant to which the recombinant vector of the above 13) is introduced;

16) a method for producing a polypeptide having an SCDase activity, which comprises:
   culturing the transformant of the above 15) to produce a polypeptide having an SCDase activity; and
   recovering the polypeptide from the culture;

17) a recombinant polypeptide having an SCDase activity encoded by the gene of the above 13), which is obtained by culturing the transformant of the above 15) to produce a recombinant polypeptide, and recovering the recombinant polypeptide from the culture;

18) a synthesized oligonucleotide probe or primer which specifically hybridizes to the gene of the above 13); and 19) an antibody or a fragment thereof obtained by using the polypeptide of the above 17) or a portion thereof, which specifically binds to the polypeptide of the above 17).

DETAILED DESCRIPTION OF THE INVENTION

Figure 1:
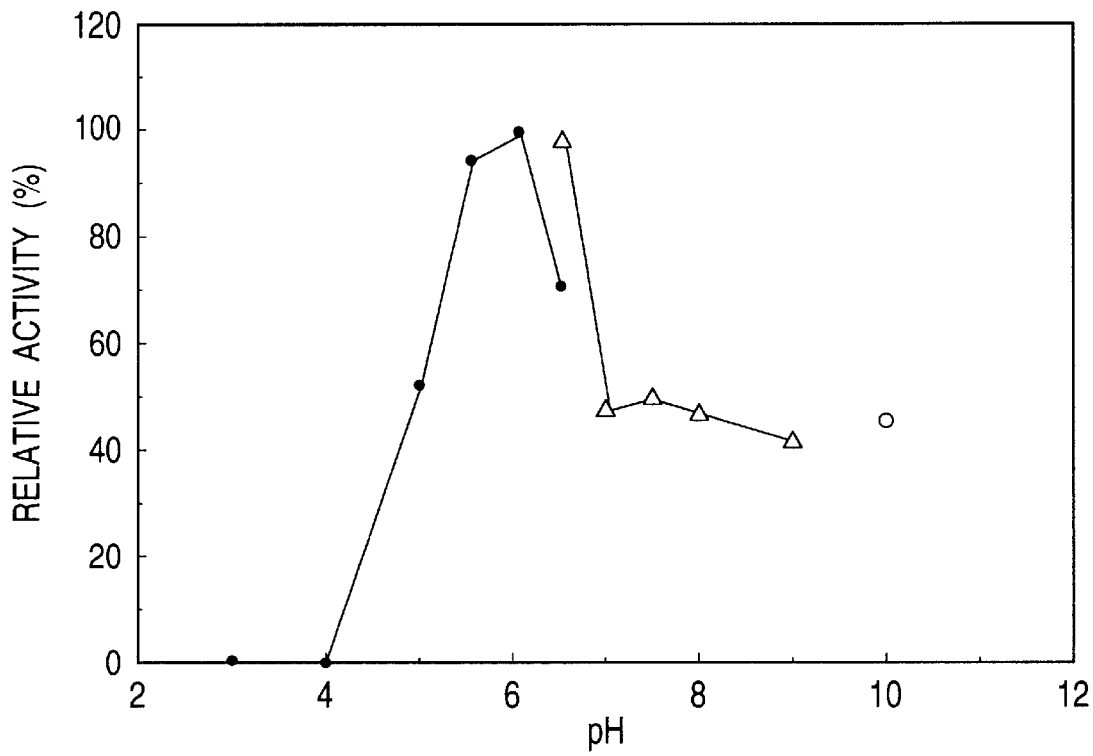
FIG. 1 is a graph which shows the optimum pH value of the SCDase obtained by the present invention.

To obtain enzymes relating to sphingolipids, the present inventors collected various samples (soil, seawater, fresh water, etc.) and subjected these samples to screening. In the course of the screening, they have surprisingly found out a novel SCDase activity unknown hitherto by which neutral glycosphingolipids and acidic glycosphingolipids can be hydrolyzed into a sphingosine base and a fatty acid, thus forming a lysoglycolipid and a fatty acid.

Furthermore, the present inventors have specified a microorganism producing the enzyme of the present invention, further purified the enzyme and clarified the physicochemical properties of the same.

Moreover, the present inventors have succeeded in obtaining a gene coding for a polypeptide having SCDase activity and continued intensive studies with the aim of elucidating its gene structure and, as a result of the efforts, have succeeded at last in elucidating complete structure of the gene coding for a polypeptide having an SCDase activity and further succeeded in producing a high purity SCDase simply and easily by means of genetic engineering techniques.

Still furthermore, the present inventors have conducted studies on a method for producing lysosphingolipids in a large amount. As a result, they have found that a lysosphingolipid can be obtained by incubating a bacterium producing an SCDase in the presence of the corresponding sphingolipid. Under these circumstances, the present inventors have newly isolated bacteria capable of converting sphingolipids into lysosphingolipids in a synthetic medium containing the sphingolipids as the carbon source. They have further found that lysosphingolipids can be obtained efficiently over a wide range without limiting to a specific sphingolipid by incubating these bacteria in the presence of sphingolipids.

Still moreover, the present inventors have conducted studies on the synthesis method of a sphingolipid or a sphingolipid derivative, and found as the result that the recombination of a fatty acid to the amino group of the sphingoid of a lysosphingolipid or the substitution of a fatty acid bonded via an acid-amide bond to the sphingoid in a sphingolipid with other fatty acid produces a sphingolipids or sphingolipid derivative by using an enzyme which acts on the acid-amide bond of the sphingoid in a sphingolipid and hydrolyzes it into a lysosphingolipid and a fatty acid.

Also, previously, a reverse reaction or transfer reaction of an enzyme must have been conducted by adding a donor in a large amount excess for an acceptor in an organic solvent system in order to prevent a simultaneously occurring hydrolysis reaction. However, the present inventors have found that a sphingolipid or sphingolipid derivative can be synthesized under mild conditions in an aqueous solution without adding a donor in a large amount excess for an acceptor by using an enzyme which can specifically hydrolyze the acid-amide bond between a sphingoid and a fatty acid in the sphingolipid, and thereby have accomplished the present invention.

Thus, the present invention has been attained based on the above findings.

The present invention will be described in detail below.

The term "sphingolipid" as used herein means natural and synthetic substances having long-chain base sphingoid and mixtures thereof, and includes glycosphingolipids, sphingophospholipid and ceramides. The term "lysosphingolipid" as used herein means the N-deacylated form of a sphingolipid from which the fatty acid bonded via an acid-amide bond to the amino group of sphingoid has been eliminated.

The aliphatic carboxylic acid as used herein involves carboxylic acids having an aliphaticity, such as acids in which a hydrocarbon chain in a fatty acid is substituted with halogen or a functional group (for example, a substituted or unsubstituted amino group, an oxo group, a hydroxyl group or the like), acids having oxygen, sulfur or an amino group in the hydrocarbon chain as well as saturated fatty acids and unsaturated fatty acids.

The term "sphingolipid ceramide deacylase (SCDase)" as used herein means an enzyme which acts on the amide bond of the sphingoid in a sphingolipid, and specifically hydrolyzes the sphingolipid into a lysosphingolipid and a fatty acid, namely, an enzyme which specifically hydrolyzes the acid-amide bond between a sphingoid and a fatty acid in a sphingolipid.

In addition, recombinant enzymes obtained using genes which encode these enzymes and recombinant enzymes obtained using genes which encode these enzymes and are modified by at least one of deletion, addition, insertion and substitution are also included in the SCDase of the present invention, with the proviso that they are enzymes which can specifically hydrolyze the acid-amide bond between a sphingoid and fatty acid in a sphingolipid.

In using the enzyme, a purified product of the enzyme or a culture broth or crude extract containing the enzyme may be used.

The "microorganism capable of producing an SCDase" as used herein includes bacteria belonging to the genus Pseudomonas or Shewanella capable of producing an SCDase. However, the present invention is not restricted thereto, any microorganisms can be used so long as they are capable of producing an SCDase. Furthermore, they include microorganisms such as bacteria, yeast's, actinomycetes, hyphomycetes, basidiomycotina, and the like, and cells derived from plants, insects, animals, and the like. In such a case, it is preferred that the SCDase thus produced acts on sphingolipids over a wide range. Such a microorganism may be isolated by, for example, the following method. A sample obtained from soil, marine algae, seawater, submarine sand, submarine mud, the contents of the digest tract of a marine organism, etc. is added to a synthetic medium containing a sphingolipid as the sole carbon source. After incubating at 25° C. for 3 to 4 days, the substrate contained in the culture supernatant is examined by TLC. Then a substance having an SCDase activity is inoculated into the same medium. After repeating these procedures several times, each colony is isolated onto a plate medium to thereby give the target microorganism.

Moreover, the "microorganism capable of producing an SCDase" as used herein involves microorganisms having a vector, to which a gene encoding an SCDase and optionally having deletion, insertion or substitution has been ligated, introduced thereinto.

An enzyme which acts on the acid-amide bond of the sphingoid in a sphingolipid and hydrolyzes it into a lysosphingolipid and a fatty acid or microorganisms capable of producing the enzyme may be immobilized on a well known solid carrier or incorporated into liposome or reversed micelle. An enzyme modified with a high molecular substance may also be used.

The term "antibody or a fragment thereof" as used herein means either a polyclonal antibody or a monoclonal antibody, with the proviso that it is an antibody or a fragment thereof which specifically binds to a recombinant polypeptide produced by the SCDase gene of the present invention. The antibody of the present invention can be easily prepared by immunizing a rabbit, a mouse and the like with the whole or a part of the polypeptide of the present invention, for example, in accordance with the method described in *Current Protocols in Immunology*, edited by John E. Coligan, John Wiley & Sons, Inc. (1992). By purifying the thus obtained antibody and then treating it with a peptidase or the like, fragments of the antibody are obtained. The thus obtained antibodies or fragments thereof can be applied, for example, to affinity chromatography, screening of various libraries (genomic DNA or cDNA), pharmaceutical drugs, diagnostic drugs, research reagents and the like.

The method for producing the SCDase of the present invention is not particularly restricted. Namely, it may be performed by using, for example, microorganisms or cells capable of producing the SCDase of the present invention. For example, Pseudomonas sp. TK-4 can be used therefor. This strain, which has been isolated from the soil for the first time by the present inventors, has the following mycological properties.

(1) Growth temperature range: to 41° C.
(2) Gram-staining: negative
(3) Morphology: bacillus
(4) Motility: positive
(5) Growth under aerobic condition: positive
(6) Growth under anaerobic conditions: negative
(7) Catalase: positive
(8) Oxidase: positive
(9) O-F test: F
(10) O/129 sensitivity test: nonsensitive
(11) Production of chromogen: +/−
(12) Growth in ammonium ion and glucose synthetic medium: positive
(13) Utilization of amino acid as carbon source: Arg, Asn, His, Glu, Ser and Ala
(14) Growth in 7.5% NaCl-containing nutrient broth: negative
(15) Butanediol dehydrogenase activity: positive
(16) Gas production from glycerol: positive
(17) Gas production from glucose: positive
(18) Evolution of hydrogen sulfide from 2.5% aqueous solution of peptone: positive
(19) Sugar metabolism: galactose, sucrose, arabinose
(20) GC content: about 69.4%
(21) Flagellum: mono polar flagellum Based on these results, this strain has been identified as one belonging to the genus Pseudomonas.

It has been named Pseudomonas sp. TK-4 and deposited in accordance with Budapest Treaty at National Institute of Bioscience and Human-Technology, Agency of Industrial Science and Technology, Ministry of International Trade and Industry [1–3 Higashi 1-chome, Tsukuba-shi, Ibaraki 305, JAPAN] under the accession number FERM BP-5096 since Jun. 24, 1994.

The enzyme of the present invention can be obtained by, for example, incubating the above-mentioned strain in a nutrient medium and, after the completion of the incubation, isolating the enzyme from the culture medium. Any nutritional sources may be added to the medium, so long as the strain can utilize the same to thereby produce the enzyme of the present invention. For example, glycerol, glucose, sucrose, molasses, etc. are usable as a carbon source, while yeast extract, peptone, corn steep liquor, meat extract, defatted soybean, ammonium sulfate, ammonium nitrate, etc. are usable as a nitrogen source. Further, inorganic matters and metal salts (for example, sodium salt, potassium salt, phosphate, magnesium salt, zinc salt) may be added thereto. It is also possible to add from 0.01 to 0.5% of a glycolipid such as asialo GM1 to the medium so as to elevate the productivity of the enzyme of the present invention. It is also preferable to add dimethylcyclodextrin to the medium to a concentration of 0.1%. When the strain capable of producing the enzyme of the present invention is incubated, the yield of the enzyme widely varies depending on the incubation conditions. It is generally preferable that the inoculum size of the strain ranges from 2 to 5%, the incubation temperature ranges from 20 to 35° C. and the pH value of the medium ranges from 5 to 8. The enzyme of the present invention can be produced by incubating the strain under aeration for 1 to 7 days. Needless to say, the incubation conditions are to be set in such a manner as to achieve the maximum productivity of the enzyme of the present invention depending on the selected strain, the composition of the medium, etc.

The enzyme of the present invention is produced extracellularly by the above-described strain. Therefore, the enzyme can be purified by subjecting the culture medium to solid/liquid separation and the resulting supernatant to a purification procedure commonly employed in the art. For example, purification may be performed by salting out, precipitation from organic solvents, ion exchange column chromatography, hydroxyapatite column chromatography, gel filtration column chromatography or freeze-drying. The purity of the enzyme can be determined by, for example, polyacrylamide gel disk electrophoresis.

The SCDase obtained by the strain has the following enzymological and physicochemical properties.

(1) Assay of Enzyme Activity

The enzyme activity of the SCDase is assayed in the following manner. To 10 µl of a substrate solution [50 mM acetate buffer solution (pH 6.0) containing 2 mM of asialo GM1 and 0.6% (w/v) of Triton X-100] is added 10 µl of an enzyme solution. After reacting at 37° C. for 30 minutes, the enzyme reaction is ceased by heating the mixture to 100° C. for 3 minutes. Then the reaction mixture is concentrated to dryness with a centrifugal concentrator. Then the obtained concentrate is dissolved in 10 µl of 50% methanol and placed on a TLC plate (silica gel 60; manufactured by Merck & Co., Inc.). After developing with chloroform/methanol/ 0.02% aqueous solution of $CaCl_2$ (5/4/1 by volume), the sphingolipid is subjected to color development by the orcinol-sulfuric acid method. With the use of this developing solvent, the sphingolipid, from which the fatty acid has been eliminated, shows an Rf value somewhat later than that of the native sphingolipid. This spot is determined by using a TLC chromatoscanner (Shimadzu CS-9000, manufactured by Shimadzu Corporation) at a wavelength of 540 nm.

One unit (1 U) of activity is defined as the amount of the enzyme liberating 1 µmol of lysoasialo GM1 per minute from asialo GM1 at 37° C.

(2) Function

It acts on a ceramide moiety in the molecule of a sphingolipid and hydrolyzes the ceramide moiety into a sphingosine base and a fatty acid, thus forming a lysosphingolipid and a fatty acid.

(3) Substrate Specificity

Sphingolipids (10 nmol each) were incubated at 37° C. for 16 h with 2 milliunits of the enzyme in 20 µl of 20 mM sodium acetate buffer, pH 5.0, containing 0.8% Triton X-100. The extent of hydrolysis was examined by TLC and calculated.

TABLE 1

| Substrate | Digestion ratio (%) |
| --- | --- |
| GM1 | 61 |
| GM2 | 69 |
| GM3 | 45 |
| GD1a | 49 |
| GQ1b | 49 |
| Gb4 | 53 |
| Asialo GM1 | 67 |
| Lac-cer | 64 |
| Glc-cer | 48 |
| Gal-cer | 42 |
| Sulfatide | 59 |
| Sphingomyelin | 28 |

(4) Optimum pH Value

As FIG. 1 shows, the enzyme of the present invention exhibits a high activity at about pH 5 to 8.5. In the assay of the activity, a 50 mM acetate buffer solution, a 50 mM phosphate buffer solution and a 50 mM glycine buffer solution are used respectively at pH 3.0 to 6.5, pH 6.5 to 9.0 and pH 10. FIG. 1 shows the optimum pH value of the enzyme of the present invention wherein the ordinate refers to the relative activity (%) and the abscissa refers to pH. In FIG. 1, ● stands for the acetate buffer solution, ∆ stands for the phosphate buffer solution and α stands for the glycine buffer solution.

(5) Optimum Temperature

Figure 2:
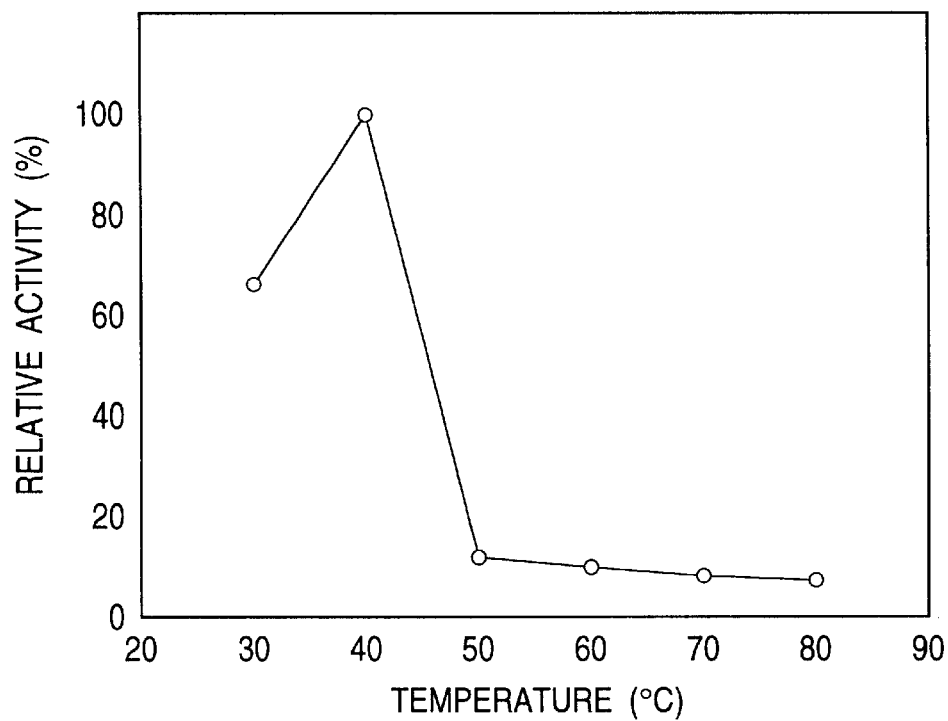
FIG. 2 is a graph which shows the optimum temperature of the SCDase obtained by the present invention.

As FIG. 2 shows, the enzyme of the present invention exhibits the maximum activity at about 40° C. That is to say, FIG. 2 shows the optimum temperature of the enzyme of the present invention wherein the ordinate refers to the relative activity (%) and the abscissa refers to the temperature (° C.)

(6) pH Stability

The enzyme of the present invention is maintained at each definite pH value at 5° C. for 16 hours. After returning the pH value to 6.0, the enzyme activity is measured to thereby examine the pH stability of the enzyme. As the buffer solution, a 50 mM acetate buffer solution, a 50 mM phosphate buffer solution, a 50 mM tris-hydrochloride buffer solution and a 50 mM glycine buffer solution are used respectively at pH 3.5 to 6.0, pH 6.0 to 8.0, pH 8.0 to 9.0 and pH 9.0 to 9.5.

Figure 3:
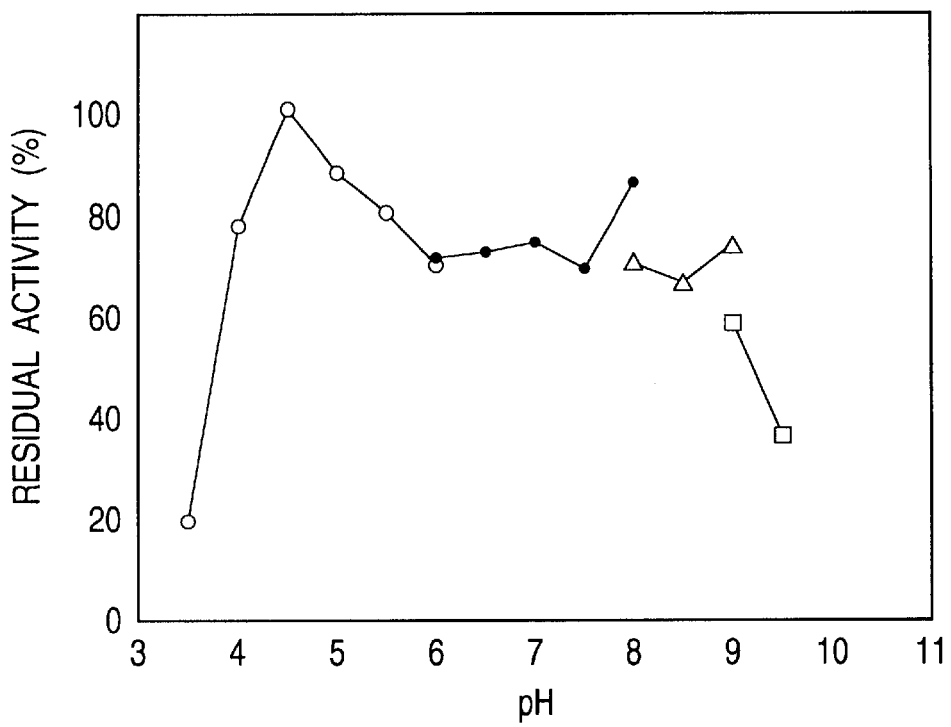
FIG. 3 is a graph which shows the pH stability of the SCDase obtained by the present invention.

As FIG. 3 shows, the enzyme of the present invention remains stable within a range of pH 4 to 9. Namely, FIG. 3 shows the pH stability of the enzyme of the present invention wherein the ordinate refers to the residual activity (%) and the abscissa refers to the pH. In FIG. 3, ○ stands for the acetate buffer solution, ● stands for the phosphate buffer solution, ∆ stands for the tris-hydrochloride buffer solution and □ stands for the glycine buffer solution.

(7) Heat Stability

Figure 4:
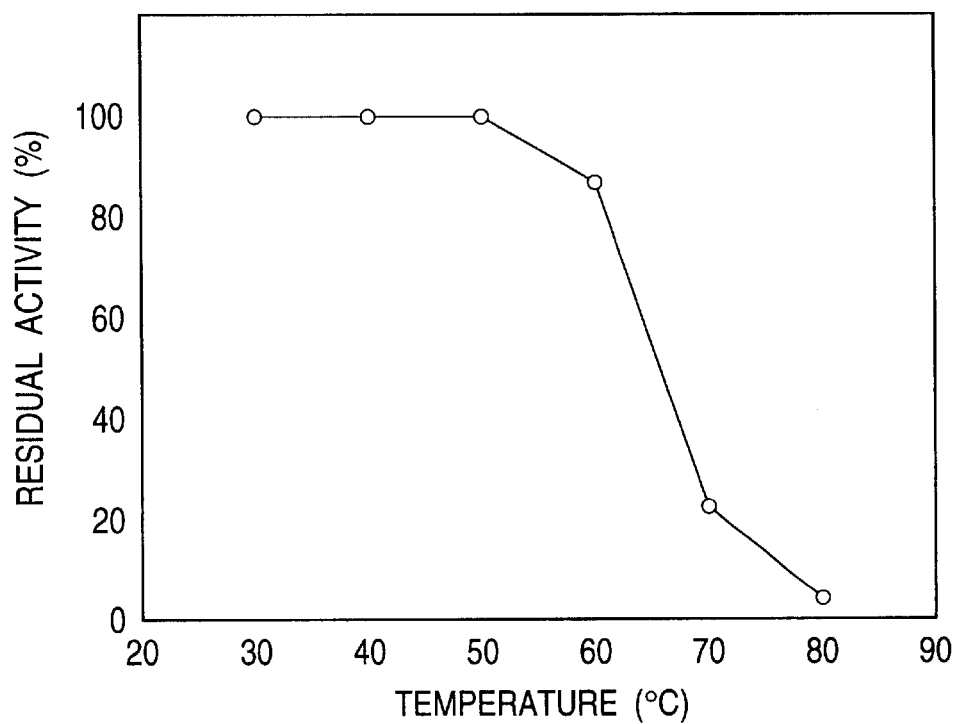
FIG. 4 is a graph which shows the heat stability of the SCDase obtained by the present invention.

An examination on the heat stability of the enzyme of the present invention indicates that it sustains 90% of the activity after treating at 60° C. for 30 minutes, as shown in FIG. 4. That is to say, FIG. 4 shows the heat stability of the enzyme of the present invention wherein the ordinate refers to the residual activity (%) and the abscissa refers to the temperature (° C.).

(8) Molecular Weight

As the result of SDS-polyacrylamide gel electrophoresis (SDS-PAGE), it is found out that the molecular weight of the enzyme of the present invention is about 52,000.

(9) Identification of the Structure of Enzyme Reaction Product

The digestion product obtained by the enzyme of the present invention is identified by digesting asialo GM1 with the enzyme, purifying the digestion product by reversed phase high performance liquid chromatography (HPLC) and then analyzing the purified product by fast atom bombardment mass spectrum (FAB-MS). Namely, 200 µl of an enzyme solution and 10 µl of toluene are added to 1 ml of a 50 mM acetate buffer solution (pH 6.0) containing 3 mg/ml of asialo GM1 (C 18:0, d 18:1, molecular weight: 1,254) and 0.6% of Triton X-100 and the mixture is reacted at 37° C. for 3 days. After the completion of the reaction, chloroform/ methanol (2/1 by volume) is added to the reaction mixture in a 5-fold amount thereof. After partition, the upper layer is recovered and evaporated to dryness. The resulting residue is dissolved in 500 µl of chloroform/methanol/water (3/48/ 47 by volume) to thereby give a sample for the reversed phase column chromatography. An ODS-80T column (column size: 4.6×75 mm, manufactured by Tosoh Corporation) is employed therein. The flow rate is set to 1 ml/min and fractions are collected in 1.5 ml portions. After adding the sample to the column, 10 ml of methanol/water (6/4 by volume) is passed therethrough. Next, gradient elution is effected until the concentration of methanol reaches 100% for 60 minutes. Finally, 5 ml of chloroform/ methanol/water (60/30/4.5 by volume) is passed through the column. Fractions of lysoasialo GM1 are collected to thereby give a purified preparation which is then subjected to the FAB-MS analysis (matrix: triethanolamine).

Figure 5:
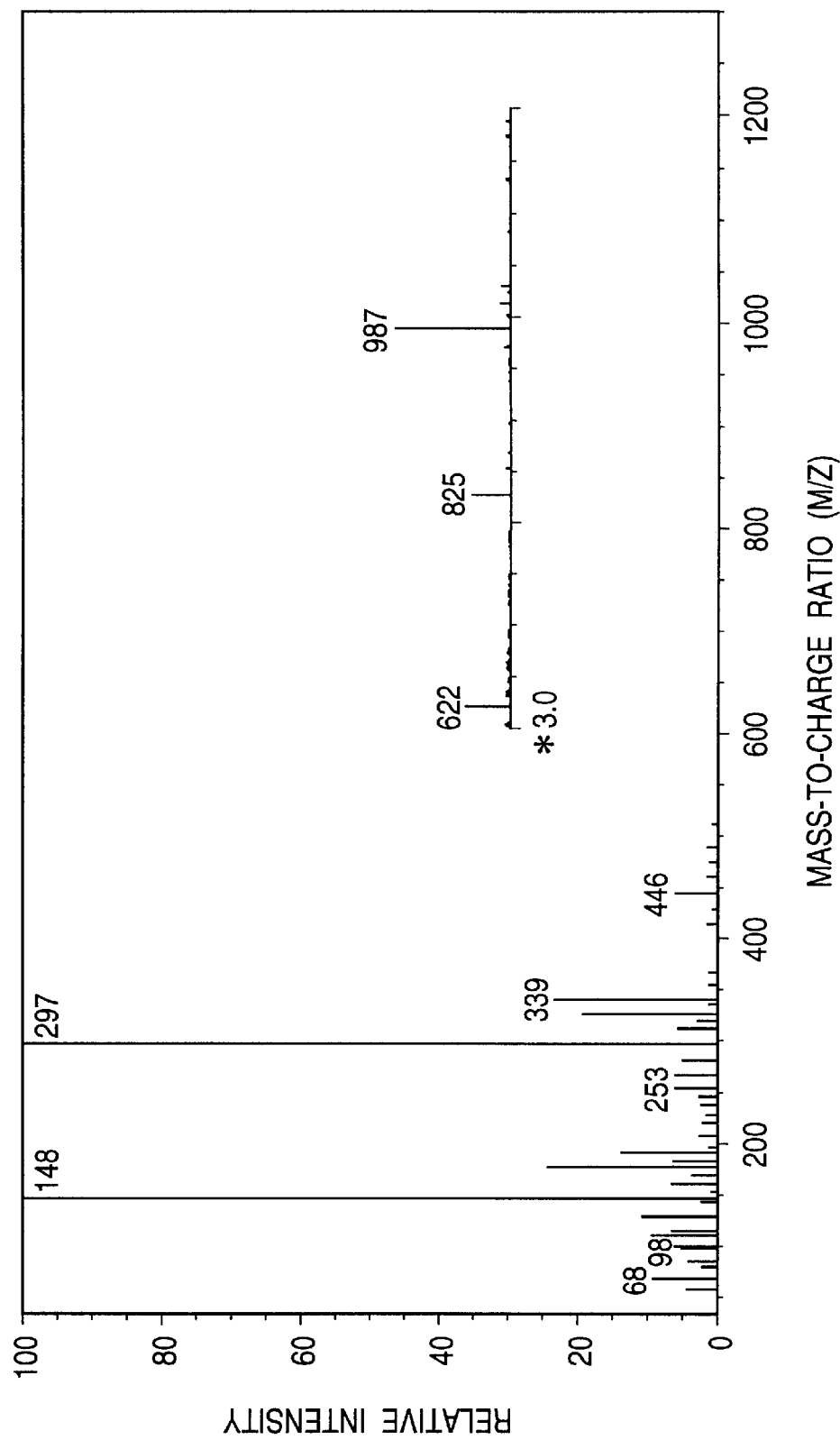
FIG. 5 is an FAB-mass spectrum of the lysoasialo GM1 obtained by digesting asialo GM1 with the use of the SCDase obtained by the present invention.

FIG. 5 shows the results. That is to say, FIG. 5 shows the FAB-MS data of the product obtained by digesting asialo GM1 with the enzyme of the present invention. In FIG. 5, the ordinate refers to the relative intensity and the abscissa refers to the mass-to-charge ratio (M/Z). An magnification [600–1200 (M/Z)] is given at the center of FIG. 5. The signal position [(M-H)⁻] of asialo GM1 (Gal-GalNAc-Gal-Glc-Cer, wherein Cer stands for ceramide; molecular weight:

1254) employed as the substrate is 1253, while that of lysoasialo GM1 (Gal-GalNAc-Gal-Glc-Sph, wherein Sph stands for sphingosine base; molecular weight: 988) formed as the digestion product is 987.

As FIG. 5 shows, signal 987 corresponding to the molecular weight 988 of lysoasialo GM1 is obtained as the strongest one. Also, FIG. 5 shows signal 825, which indicates that Gal has liberated from the nonreducing end of the carbohydrate chain moiety of lysoasialo GM1, and another signal 622, which indicates that N-acetylgalactosamine (GalNAc) has further liberated therefrom. Based on these data, it is suggested that the product of the reaction by the enzyme of the present invention is a lysoglycolipid having the carbohydrate chain moiety of asialo GM1 in its carbohydrate chain moiety.

In addition to the results of the FAB-MS analysis as described above, there have been proved the following facts.
(I) The product obtained by the digestion with the enzyme of the present invention is positive in the ninhydrin reaction.
(II) The carbohydrate chain moiety of asialo GM1 is formed by treating this product with endoglycoceramidase (EC. 3.2.1.123) which is an enzyme capable of hydrolyzing a glycoside bond between a carbohydrate chain and a ceramide or a carbohydrate chain and a sphingosine.
(III) This carbohydrate chain moiety is negative in the ninhydrin reaction, which indicates that the acetyl group of GalNAc has not liberated therefrom.

As a result of analyzing a nucleotide sequence of a gene encoding the enzyme of the present invention, the amino acid sequence of the enzyme has been obtained. SEQ ID NO:1 in the Sequence Listing shows one example of the amino acid sequence of the enzyme of the present invention. The enzyme which comprises an amino acid sequence wherein at least one of deletion, addition, insertion and substitution in one or plural amino acid residues is conducted in the amino acid sequence represented by SEQ ID NO:1 is included in the scope of the present invention so long as it has an SCDase activity.

*Shewanella alga* NS-589 is a strain newly found by the present inventors from the soil in tidal flat Wajiro in Fukuoka prefecture, Japan. It has the following mycological properties.
(1) Morphology: bacillus
(2) Gram-staining: −
(3) Spore: −
(4) Motility: +
(5) Flagellum: very short
(6) Attitude to oxygen: aerobic
(7) Oxidase: +
(8) Catalase: +
(9) O-F test: O
(10) Colony color: yellowish
(11) $Na^+$ requirement: +
(12) Salt requirement
  Growth in medium containing 0% of NaCl: −
  Growth in medium containing 1% of NaCl: +
  Growth in seawater medium: +
(13) DNA degradation: +
(14) Arginine dehydrolase: −
(15) Ornithine decarboxylase: +
(16) Lysine decarboxylase: −
(17) Formation of hydrogen sulfide: +
(18) Growth in the presence of 6% of NaCl: +
(19) Growth temperature
  Growth at 4° C.: −
  Growth at 37° C.: +
  Growth at 42° C.: +
(20) Growth in SS agar medium: +
(21) Formation of acid
  D-Ribose: +
  Maltose: −
  L-Arabinose: −
(22) GC content: 53%
(23) Quinone: Q-8, Q-7, MK-7 and MMK-7

Based on these results, this strain is identified as one belonging to *Shewanella alga* in accordance with *Bergey's Manual of Systematic Bacteriology*, 1, Williams & Wilkins Company (1984); *System and Applied Microbiology*, 6:171 (1985); and *International Journal of Systematic Bacteriology*, 42:628 (1992).

This strain was named *Shewanella alga* NS-589 and has been deposited at the above-identified National Institute of Bioscience and Human-Technology, Agency of Industrial Science and Technology under the accession number FERM P-15700.

The SCDase produced by this strain has the following enzymological and physicochemical properties.
(1) Action
Acting on a ceramide moiety in the molecule and hydrolyzing it into a sphingosine base and a fatty acid, thus forming a lysosphingolipid and a fatty acid.
(2) Substrate Specificity
Acting on acidic glycolipids (GM1, GM2, GD1a, GD1b, sialosyl paragloboside, etc.), neutral glycolipids (lactosyl ceramide, Gb4, Gb5, etc.), sulfated glycolipids (sulfatide, etc.) and sphingomyelin which is a sphingophospholipid, thus forming the corresponding lysosphingolipid and fatty acid in each case.

The substrate specificity was examined as follows. *Shewanella alga* NS-589 was inoculated into a synthetic medium (dipotassium hydrogenphosphate 0.05%, ammonium chloride 0.05%, sphingomyelin 0.1%, sodium taurodeoxycholate 0.1%, sodium chloride 2%, 2,6-O-dimethyl-β-cyclodextrin 0.1%; pH 7.4). Two days after shaking cultivation at 30° C., the strain was removed to obtain a supernatant by centrifuge. A 50 mM acetate buffer (2 μl; pH 6.0) containing 3 μl of the supernatant and 1.6% Triton X-100 was allowed to react with 5 μl of 1.2 mM of each of sphingolipids shown in Table 2 at 37° C. for 16 hours, and then the resulting mixture was analyzed with a thin layer chromatography.

The digestion ratios of various substrates by a crude SCDase obtained from *Shewanella alga* NS-589.

TABLE 2

| Substrate | Digestion ratio (%) |
| --- | --- |
| GM1 | 30.6 |
| GM2 | 13.9 |
| GD1a | 32.6 |
| GT1b | 26.2 |
| Sialyl palagloboside | 36.8 |
| Lactosylceramide | 19.3 |
| Gb4 (Gb4-cer) | 32.2 |
| Gb5 (Gb5-cer) | 39.4 |

Figure 7:
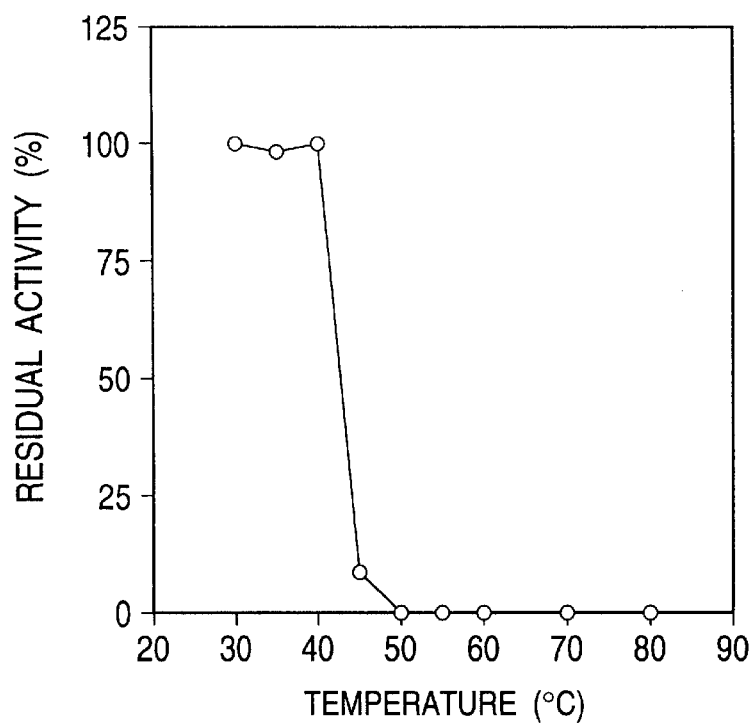
FIG. 7 is a graph which shows the optimum pH value of the SCDase produced by the bacterium of the genus Shewanella of the present invention.

(3) Optimum pH Value and Temperature Stability
Having an optimum pH value range of from 7 to 8 and showing a relatively high activity at pH 5 to 8.5 [see FIG. 7 wherein the ordinate refers to relative activity (%) while the abscissa refers to pH value, □ stands for an acetate buffer, ◇ stands for MOPS and ○ stands for a glycine buffer].

When stored at various temperatures for 15 minutes, this enzyme is almost completely inactivated at 50° C. or above but remains stable at relatively low temperatures (40° C. or below) [see FIG. 9 wherein the ordinate refers to residual activity (%) while the abscissa refers to temperature (° C.)].

Based on these results, it has been clarified that the enzyme of the present invention acts on a ceramide moiety in the molecule of a sphingolipid and hydrolyzes the ceramide moiety into a sphingosine base and a fatty acid, thus catalyzing a reaction for the formation of a lysosphingolipid and a fatty acid.

The isolated gene which encodes a polypeptide having an SCDase activity of the present invention is specifically described by using cloning of the SCDase gene prepared from Pseudomonas sp. TK-4 as an example.

(1) Firstly, Pseudomonas sp. TK-4 or an SCDase high production strain obtained by simply purifying Pseudomonas sp. TK-4 (for example, by selecting it on a plate medium) is cultured in accordance with the method described in *Journal of Biological Chemistry*, 270:24370–24374 (1995), and an SCDase is isolated and purified from the resulting culture.

(2) Next, information on partial amino acid sequences of the thus purified SCDase is obtained. In order to determine the partial amino acid sequences, the purified SCDase may be subjected directly to amino acid sequence analysis (for example, using Protein Sequencer 476A manufactured by Applied Biosystems) in the conventional way by the Edman degradation method [*Journal of Biological Chemistry*, 256:7990–7997 (1981)] or it may also be effective to carry out limited hydrolysis of the SCDase using a protease having a high specificity, such as lysylendopeptidase, N-tosyl-L-phenylalanyl chloromethyl ketone (TPCK)-trypsin or the like, followed by separation and purification of the thus obtained peptide fragments using a reverse phase HPLC and the like and subsequent amino acid sequence analysis of the thus purified peptide fragments.

(3) The SCDase gene is then cloned on the basis of the thus obtained information of partial amino acid sequences. Generally, a method using the polymerase chain reaction (PCR) or a hybridization method can be used.

For example, the hybridization method may be carried out in the following manner.

a) Based on the information on partial amino acid sequences, a synthetic oligonucleotide is designed as a probe for the Southern hybridization.

b) Separately from the above a), genomic DNA of Pseudomonas sp. TK-4 is completely digested with appropriate restriction enzymes, and the resulting fragments are separated by agarose gel electrophoresis and blotted on a nylon membrane in the conventional way.

c) Hybridization of the thus separated DNA fragments with the synthetic oligonucleotide probe designed based on the information on partial amino acid sequences is carried out generally under conventional conditions. For example, the nylon membrane is subjected to a blocking reaction in a hybridization solution containing salmon sperm DNA and then incubated overnight at a constant temperature by adding each synthetic oligonucleotide probe labeled with $^{32}$p. The thus treated nylon membrane is washed and then subjected to autoradiography to detect a DNA fragment which hybridizes to the synthetic oligonucleotide probe. A DNA fragment which corresponds to the detected band is extracted from the gel and purified.

d) The thus obtained DNA fragment which hybridizes to the synthetic oligonucleotide probe is inserted into a plasmid vector in the conventional manner. Although not particularly limited, pUC18, pUC19, pUC119, pTV118N or the like can be used suitably as the plasmid vector.

e) Next, transformation of a host is carried out by introducing the thus obtained recombinant plasmid into the host. When *Escherichia coli* is used as the host, either a wild strain or a mutant strain can be used as the *Escherichia coli* host, with the proviso that it has the transformation ability. With regard to the introduction method, any usually conventional method such as the method described at page 250 in *Molecular Cloning, A Laboratory Manual* (T. Maniatis et al., Cold Spring Harbor Laboratory (1982)) can be used.

f) Next, a transformant having the DNA fragment of interest is selected. For this purpose, characteristics of the plasmid vector are used. In the case of pUC19, for example, colonies having introduced exogenous gene are selected by picking up a colony which shows ampicillin resistance on a plate medium containing ampicillin or a colony that shows ampicillin resistance and white color on a plate medium containing ampicillin, 5-bromo-4-chloro-3-indolyl-β-D-galactoside (X-gal) and isopropyl-β-D-thiogalactopyranoside (IPTG).

g) A colony having the vector containing the DNA fragment of interest is selected from the thus collected colonies. As the selection method, colony hybridization or plaque hybridization is optionally used depending on the type of vector. Alternatively, PCR may also be used.

h) When a vector containing the DNA fragment of interest is selected, nucleotide sequence of the DNA fragment of interest inserted into the vector is determined by a usually used method such as the dideoxy chain terminator method described in *Proceedings of the National Academy of Science of the USA*, 74:5463–5467 (1977). The thus determined nucleotide sequence is compared with N-terminal amino acid sequence, partial amino acid sequence, molecular weight and the like of SCDase to determine whether the thus obtained DNA fragment is the complete length or a partial length of the SCDase gene of interest. The structure and the whole amino acid sequence of SCDase are determined based on the thus obtained DNA fragment containing thus-obtained SCDase gene.

i) When the vector containing the DNA fragment of interest does not have the full length of the SCDase gene, the full length of the SCDase gene of interest can be obtained by digesting the above-described Pseudomonas sp. TK-4 genomic DNA with other restriction enzymes, obtaining the deleted portions from the thus prepared digests by, for example, a hybridization method using the just obtained DNA fragment or a part thereof as a probe and then ligating the deleted portions with the DNA fragment.

When PCR is employed, it can for example be carried out in the following manner.

When cloning of the SCDase gene of the present invention originated from the Pseudomonas sp. TK-4 strain of the present invention was carried out, it was found that a portion of the gene of interest can be amplified by carrying out PCR using a synthetic oligonucleotide primer designed on the basis of the information on partial amino acid sequences of SCDase and using the genomic DNA as the template.

Firstly, the gene fragment of interest is obtained by carrying out PCR using the genomic DNA of Pseudomonas sp. TK-4 as the template and using a synthetic oligonucleotide primer designed on the basis of the information on partial amino acid sequences. That is, a synthetic oligonucleotide primer-1 (SEQ ID NO:4) and a synthetic oligonucleotide primer-2 (SEQ ID NO:5), designed from an N-terminal amino acid sequence N (SEQ ID NO:3), and a synthetic oligonucleotide primer-3 (SEQ ID NO:7) designed from a partial amino acid sequence N-8 (SEQ ID NO:6) are respectively synthesized.

In this case, two different oligonucleotide primers are designed and synthesized for leucine because of the presence of many codons for this amino acid. Additionally, in order to facilitate determination of the nucleotide sequence of the amplified PCR product, a nucleotide sequence of a restriction enzyme site such as EcoRI site is added in advance to the 5'-end side of each primer.

PCR is carried out in accordance with the method described in *PCR Technology* (edited by Erlich HA, Stockton Press, 1989).

For example, this method may be carried out using GeneAmp™ Reagent Kit (manufactured by Perkin-Elmer) by a total of 30 cycles of the reaction consisting of 94° C. for 0.5 minute, 50° C. for 1 minute and 72° C. for 1 minute.

By one PCR using the genomic DNA of Pseudomonas sp. TK-4 as the template and using a combination of the primer-1 (SEQ ID NO:4) or primer-2 (SEQ ID NO:5) with the primer-3 (SEQ ID NO:7), a specific band which seems to be an amplified DNA fragment is detected by agarose gel electrophoresis.

When the nucleotide sequence of this amplified DNA fragment is determined by a conventional method such as the dideoxy chain terminator method, a sequence corresponding to a partial amino acid sequence of the SCDase can be found in the thus determined sequence, in addition to the synthetic oligonucleotide primer sequences, so that a portion of the SCDase gene of interest can be obtained. As a matter of course, a gene encoding the full length of the SCDase can be cloned by further carrying out a hybridization method or the like using the thus obtained gene fragment as a probe.

A full nucleotide sequence of the gene which encodes the SCDase derived from Pseudomonas sp. TK-4, obtained in this manner, is represented by SEQ ID NO:2, and corresponding amino acid sequence deduced therefrom is represented by SEQ ID NO:1. In addition to the sequence represented by SEQ ID NO:2, there are a large number of other nucleotide sequences corresponding to the amino acid sequence represented by SEQ ID NO:1, and all of these sequences are included within the scope of the present invention.

Also, the SCDase gene of the present invention includes genes which contain a portion of the amino acid sequence of SEQ ID NO:1 and encode a polypeptide having an SCDase activity; genes which contain a portion of the nucleotide sequence of SEQ ID NO:2 and encode a polypeptide having an SCDase activity; and genes which hybridize to these genes under stringent conditions and encode a polypeptide having an SCDase activity.

The term "under stringent conditions" as used herein means, for example, the following conditions. That is, the conditions under which these genes are incubated for 4 hours to overnight at 50 to 65° C. in 6 ×SSC (1×SSC is a solution containing 0.15 M NaCl and 0.015 M sodium citrate having a pH value of 7.0) supplemented with 0.5% SDS, 5×Denhartz's (0.1% bovine serum albumin (BSA), 0.1% polyvinyl pyrrolidone, 0.1% Ficoll 400) and 100 µg/ml of salmon sperm DNA.

When the full length or a portion of the SCDase gene whose complete nucleotide sequence was revealed in thus manner is used as a probe, a DNA fragment having a high homology with the SCDase gene can be selected from a genomic DNA library or cDNA library prepared from organisms other than Pseudomonas sp. TK-4.

Hybridization can be carried out under the above-described stringent conditions. For example, a genomic DNA library or cDNA library prepared from organisms other than Pseudomonas sp. TK-4 is fixed on a nylon membrane, and the thus treated nylon membrane is subjected to a blocking reaction at 65° C. in a pre-hybridization solution containing 6×SSC, 0.5% SDS, 5×Denhartz's and 100µg/ml of salmon sperm DNA. Thereafter, each probe labeled with $^{32}P$ is added thereto and incubated overnight at 65° C. The thus treated nylon membrane is washed in 6×SSC for 10 minutes at room temperature, in 2×SSC containing 0.1% SDS for 10 minutes at room temperature and then in 0.2×SSC containing 0.1% SDS for 30 minutes at 45° C. and then subjected to an autoradiography to detect a DNA fragment which specifically hybridizes to the probe. Also, genes having various homology can be obtained by changing conditions such a as washing and the like.

On the other hand, a primer for PCR can be designed from the nucleotide sequence of the gene of the present invention. By carrying out PCR using this primer, a gene fragment having a high homology with the gene of the present invention can be detected, and the whole gene can also be obtained.

In order to confirm whether or not the thus obtained gene is a gene which encodes the polypeptide of interest having an SCDase activity, it may be deduced from its gene structure and homology by comparing the determined nucleotide sequence with the nucleotide sequence of the SCDase gene of the present invention or amino acid sequence of the enzyme.

Alternatively, the presence of a gene which encodes the polypeptide of interest having an SCDase activity can be confirmed by producing a polypeptide corresponding to the obtained gene and measuring the SCDase activity using the method described below.

The following method is convenient for the production of a polypeptide having an SCDase activity using the SCDase gene of the present invention.

A polypeptide having an SCDase activity can be produced by firstly carrying out transformation of a host using a vector which contains the SCDase gene of interest and then culturing the resulting transformant under usually used conditions. In some cases, the polypeptide may be produced in the form of an inclusion body.

With regard to the host, microorganisms, animal cells, plant cells and the like can be used.

Expression of the polypeptide can be confirmed by using an antibody specific for SCDase or, when SCDase is expressed as a fused body with other polypeptide, by using an antibody specific for its polypeptide moiety.

For example, the expressed product can be confirmed by applying a recombinant *Escherichia coli* extract to SDS-polyacrylamide gel electrophoresis, transferring the gel on a polyvinylidene fluoride (PVDF) membrane and then detecting the product on the membrane using an antibody.

Alternatively, it may be convenient to confirm expression of the product by measuring the SCDase activity. Measurement of the activity can be carried out in accordance, for example, with the method described in *Journal of Biological Chemistry,* 270:24370–24374 (1995), using a recombinant *Escherichia coli* cell extract as an enzyme solution.

Once expression of the SCDase of interest is confirmed, when the transformant is *Escherichia coli*, for example, SCDase can be produced efficiently by determining conditions for the optimum expression of the SCDase, such as medium compositions, medium pH, culturing temperature, amount and applying period of an inducer to be used, culturing time and the like.

A conventional method can be employed for purifying the SCDase from the resulting culture of the transformant.

When the transformant is an *Escherichia coli* strain, the expressed product may be formed in the form of an insoluble inclusion body. In that case, the cells after completion of the culturing are recovered by centrifugation, disrupted by an ultrasonic treatment or the like, and then subjected, for example, to centrifugation to recover an insoluble fraction containing the inclusion body. After washing of the inclusion body, a polypeptide which keeps the SCDase activity of interest can be obtained by solubilizing the inclusion body using a conventional protein solubilizing agent such as urea, guanidine hydrochloride or the like, if necessary further purifying it by various chromatography such as ion exchange chromatography, gel filtration chromatography, hydrophobic interaction chromatography, affinity chromatography and the like, and then carrying out refolding of the polypeptide by employing dialysis, dilution or the like.

If necessary, a high purity polypeptide having an SCDase activity can be obtained by further purifying the product through various chromatography.

The expressed product may sometimes be secreted outside the transformant cells depending on each transformant used, and, in that case, the product may be purified from the culture supernatant in the same manner.

If the SCDase produced by a transformant is accumulated inside the cells, it coexists with other various intracellular enzymes and proteins but can be purified quite easily, because the amount of these impurities is very small in comparison with that of the SCDase. Also, if the SCDase is secreted outside the cells, it coexists with medium components and the like, but these impurities generally contain almost no proteinous substances which interfere purification of the SCDase, so that such an extracellular production has an advantage in that it does not require special separation and purification steps necessary for the purification of the SCDase from the culture mixture of Pseudomonas sp. TK-4.

Additionally, since the primary structure of the SCDase and its gene structure was found in the present invention, a gene in which at least one of deletion, addition, insertion or substitution occurs in one or plural amino acid residues in the amino acid sequence of natural SCDase can be produced by introducing a random mutation or a site-specific mutation. As a result, a gene encoding an SCDase which has an SCDase activity having slightly different properties such as changed optimum temperature, stable temperature, optimum pH, stable pH and the like, and the production of these SCDase varieties is possible by genetic engineering techniques.

Examples of the method for introducing random mutation include a chemical DNA treating method in which a transition mutation that causes transition of cytosine base into uracil base is induced by the action of sodium hydrogensulfite [*Proceedings of the National Academy of Sciences of the USA,* 79:1408–1412 (1982)], a biochemical method in which a base substitution is induced during the process of double-strand synthesis in the presence of [α-S] DNTP [*Gene,* 64:313–319 (1988)] and a PCR-employed method in which accuracy of the nucleotide incorporation is reduced by carrying out PCR in the presence of manganese in the reaction system [*Analytical Biochemistry,* 224:347–353 (1995)].

Examples of the method for introducing site-specific mutation include a method in which amber mutation is used [gapped duplex method, *Nucleic Acids Research,* 12:9441–9456 (1984)], a method in which restriction enzyme recognition sites are used [*Analytical Biochemistry,* 200:81–88 (1992), *Gene,* 102:67–70 (1991)], a method in which dut (dUTPase) and ung (uracil DNA glycosylase) mutation is used [Kunkel method, *Proceedings of the National Academy of Sciences of the USA,* 82:488–492 (1985)], a method in which amber mutation is induced using a DNA polymerase and a DNA ligase [oligonucleotide-directed dual amber (ODA) method, *Gene,* 152:271–275 (1995), JP-A-7-289262], a method in which a DNA repair system-introduced host is used (JP-A-8-70874), a method in which a protein that catalyzes a DNA chain exchange reaction is used (JP-A-8-140685), a method in which PCR is carried out using two different mutation introducing primers having added restriction enzyme recognition sites (U.S. Patent 5,512,463), a method in which PCR is carried out using a double-stranded DNA vector having an inactivated drug-resistance gene and two primers [*Gene,* 103:73–77 (1991)] and a method in which PCR is carried out using amber mutation (International Publication WO 98/02535).

Furthermore, the site-specific mutation can be induced easily by using a commercially available kit. Examples of the commercially available kit include Mutan™-G (manufactured by Takara Shuzo) in which the gapped duplex method is used, Mutant™-K (manufactured by Takara Shuzo) in which the Kunkel method is used, Mutan™-Express Km (manufactured by Takara Shuzo) in which the ODA method is used and QuickChange™ Site-Directed Mutagenesis Kit (manufactured by STRATAGENE) in which a mutation introducing primer and a DNA polymerase derived from *Pyrococcus furiosus* are used, as well as TaKaRa LA PCR in vitro Mutagenesis Kit (manufactured by Takara Shuzo), Mutan™-Super Express Km (manufactured by Takara Shuzo) and the like in which PCR is used.

Thus, the primary structure and gene structure of the SCDase are provided by the present invention. Also, a polypeptide having an SCDase activity can be produced with a low cost and high purity by genetic engineering techniques.

Also, since the structure of the SCDase gene was found in the present invention, a synthetic oligonucleotide probe or primer derived from the SCDase gene of the present invention, which is capable of specifically hybridizing to the SCDase, is useful for the screening, detection, amplification or the like of the SCDase gene.

Moreover, an antibody or a fragment thereof prepared using the recombinant polypeptide of the present invention or a part thereof, which is capable of specifically binding to the recombinant polypeptide of the present invention, is useful for the screening, detection, purification or the like of the SCDase.

Lysosphingolipids from which an acid-amide bonded fatty acid in the sphingolipid is removed can be produced by treating the sphingolipid with the SCDase of the present invention. If the lysosphingolipids are produced by using the enzyme of the present invention, any sphingolipids can be used as a substrate so long as they can be treated by the enzyme of the present invention. Examples of the substrate include acidic glycolipids (for example, GQ1, GT1, GD1, GD3, GM1, GM3, and the like), neutral glycolipids (for example, globoside, asialo GM1, cerebrodie and the like), sphingophospholipid (for example, sphingomyelin, and the like), sulfated glycolipids (for example, sulfatide, and the like), and the like. Lysosphingolipids can be produced by suspending these substrates in a buffer, and treating them with the enzyme of the present invention. Although the reaction conditions are not particularly limited, for example, a reaction solution is prepared at a substrate concentration of 1 to 20 mg/ml, an enzyme concentration of 1 mU to 10 U and a pH of 5.0 to 6.0, and the reaction is conducted at 37 to 40° C. Furthermore, about 0.2 to 2% surfactant, such as Triton X-100, sodium taurodeoxycholate and the like, may be added to the reaction solution.

After the completion of the reaction, the lysosphingolipid produced can be separated and purified from impurities by reverse phase column chromatography, silica gel chromatography, ion-exchange chromatography and the like. For example, when lysoasialo GM1 is purified, ODS reverse column chromatography using chloroform/methanol/water (5/4/1 by volume) as an eluent is preferred. In the chromatography, detection of the lysosphingolipid in the eluent can be monitored by thin layer chromatography (TLC). As a developing solvent of TLC, chloroform/methanol/10% acetic acid (5/4/1 by volume) can be used. The detection of substances developed on TLC can be carried out by the orcinolsulfuric acid method for a glycolipid and a lysoglycolipid, by the Coomassie Brilliant Blue method for a sphingomyelin and a lysosphingomyelin, and by the ninhydrin method for a lysosphingolipid.

In the process for producing a lysosphingolipid of the present invention, the above-mentioned strain capable of producing an SCDase is incubated in, for example, a nutrient medium and then a sphingolipid is added to the medium. Alternatively, the strain may be incubated in a nutrient medium already containing a sphingolipid. According to this method, a lysosphingolipid can be produced at high efficiency without purifying the enzyme.

The medium to be used herein is not particularly restricted, so long as the strain can grow therein and produce the SCDase and thus the target lysosphingolipid can be efficiently formed from the sphingolipid contained in the medium. As the carbon source in the medium, it is appropriate to use gangliosides which are glycosphingolipids (e.g., GQ1, GT1, GD1, GD3, GM1, GM3 and the like), neutral glycolipids (e.g., globoside, asialo GM1, cerebrodie and the like), sulfated glycolipids, sphingomyelin which is a sphingophospholipid or mixtures thereof. As the nitrogen source, use can be made of, for example, ammonium chloride, polypeptone and yeast extract. The medium may further contain inorganic matters such as phosphates, potassium salts, magnesium salts or zinc salts, metal salts and surfactants. These components are appropriately selected depending on the strain employed.

When this strain is incubated, the yield of the SCDase and the amount of the lysosphingolipid thus formed widely vary depending on the incubation conditions. In general, it is preferable that the incubation is performed at a temperature of from 20 to 35° C. at a pH value of the medium of 6 to 8 under aeration-agitation for 1 to 7 days. Thus, the lysosphingolipid of the present invention can be produced.

The present inventors have found that the yield of the target product can be elevated by performing the above-mentioned incubation in the coexistence of methylated β-cyclodextrin. Although the location(s) and number of the methyl group(s) are not restricted, 2,6-O-dimethyl-β-cyclodextrin is a particularly preferable one among all.

After the completion of the incubation, the insoluble matters including the cells are eliminated from the culture medium containing the target lysosphingolipid by centrifugation, filtration, etc. From the culture supernatant thus obtained, proteins and salts are eliminated by a method commonly employed in the art. For example, it is effective that the culture supernatant is loaded onto a reversed phase column, etc. to thereby carry out the elimination of the proteins and desalting at the same time. The culture supernatant thus desalted is then subjected to, for example, reversed phase chromatography, normal phase silica gel column chromatography or ion exchange chromatography in a conventional manner so as to purify the lysosphingolipid. The structure of the purified lysosphingolipid can be confirmed by an analytical method such as thin layer chromatography, liquid chromatography, mass spectrometry or nuclear magnetic resonance spectrometry. By incubating a sphingolipid together with the microorganism to be used in the present invention as described above, the sphingolipid can be converted into the target lysosphingolipid.

As described above, a lysosphingolipid can be produced using the enzyme of the present invention.

Next, a process for producing a lysosphingolipid derivative by treating a lysosphingolipid will be illustrated below.

As an example of the treatment, re-acylation may be cited. Acylation can be performed by a chemical or enzymatic method of acid amidation of amino group in a conventional manner.

In the chemical method, the reaction may be carried out by using an aliphatic carboxylic acid, which has been optionally labeled, or a reactive derivative thereof.

The aliphatic carboxylic acid usable in the present invention involves not only saturated and unsaturated fatty acids but also fatty acids with hydrocarbon chain substituted with a halogen or a functional group such as a substituted or unsubstituted amino group, an oxo group or a hydroxyl group and carboxylic acids with hydrocarbon chain with aliphatic nature such as acids having an oxygen, a sulfur, an amino group or the like in the hydrocarbon chain. For example, an acylated derivative can be obtained by esterifying a fatty acid and N-hydroxysuccinimide and reacting the resulting product with a lysosphingolipid in the presence of dicyclohexylcarbodiimide to introduce a fatty acid thereto. Alternatively, a fatty acid chloride may be synthesized and reacted with a lysosphingolipid to introduce a fatty acid thereto.

Another example of the treatment is a method which comprises labeling the amino group of the sphingoid in a lysosphingolipid. The labeling may be performed by introducing a substance capable of forming a chromophore, a fluorescent substance, biotin, a radioisotope or the like into the part to be labeled. Examples of fluorescent substances include dansyl chloride, 4-fluoro-7-nitrobenzofurazan (NBD-F), 10-pyrenedecanic acid, and the like. Furthermore, after a fatty acid having an ω-amino group is introduced into a lysosphingolipid by the above reacylation, a labeled compound is introduced into the ω-amino group to obtain a labeled compound having a sphingolipid structure nearer to that of natural one.

On the other hand, the enzymatic method for reacylating a lysosphingolipid may include a method using a known lipase. However, it is not specific for the amino group of a sphingoid. Additionally, examples of the enzyme which is usable for the reacylation include SCDases produced by a microorganism belonging to the genus Pseudomonas as enzymes which broadly act on a sphingolipid including a glycosphingolipid (ganglioside, neutral glycolipid) and a sphingophospholipid (sphingomyelin) [SCDase, *Journal of Biological Chemistry,* 270:24370–24374 (1995), European Patent 707063 A1 (1996)], ganglioside ceramidases produced by a microorganism belonging to the genus Nocardia as enzymes which act on only ganglioside [*Journal of Biochemistry,* 103:1–4 (1988), U.S. Pat. No. 4,997,760, U.S. Pat. No. 5,143,841], enzymes which are produced by a microorganism belonging to the genus Rhodococcus and act on only neutral glycolipid to produce the lyso-form (JP-A-6-78782), glycosphingolipid ceramide deacylases produced by a microorganism belonging to the genus Streptomyces as a enzyme which acts on a glycosphingolipid [*Bioscience, Biotechnology, and Biochemistry,* 59:2028–2032 (1995), JP-A-7-107988], and ceramidases which act on a ceramide (acylsphingosine deacylase, EC 3.5.1.23) [*Journal of Biological Chemistry*, 241:3731–3737 (1966), *Biochemistry*, 8:1692–1698 (1969) *Biochimica Biophysica Acta*, 176:339–347 (1969), Science, 178:1100–1102 (1972)]. However, the present invention is not limited thereto. As an especially usable method, the method uses an enzyme which specifically hydrolyzes an acid-amide bond of a sphingoid and a fatty acid in a sphingolipid or a microorganism capable of producing the enzyme.

The above SCDase of the present invention has a property especially suitable for the enzymatic production of a sphingolipid derivative. In the enzymatic production method of the sphingolipid or sphingolipid derivative of the present invention, generally, the reaction of the present invention progresses in a buffer solution containing sphingolipid or lysosphingolipid to be used as the material, an aliphatic carboxylic acid having or free of a marker and any one of a purified enzyme, a crude extract, a culture broth and a microorganism. The marker as used herein includes a chromophore, a fluorescent substance, biotin, radioisotope, and the like. The amount of these materials to be used is not particularly limited, and they can be used to their saturation amount. Generally, it is preferred that the aliphatic carboxylic acid is present in excess amount; however, according to the present invention, the reaction of the sphingolipid or lysosphingolipid with the aliphatic carboxylic acid progresses even at a molar ratio of 1:1, and the sphingolipid or lysosphingolipid may be present in excess amount.

Also, the amount of an enzyme or a microorganism which produces the enzyme is not particularly limited and can be selected at will within a broad range. It may be used, for example, in an approximate amount of 0.1 mU or more, preferably from 0.5 mU to 10 mU, per 1 ml of the starting solution. As the buffer solution, any appropriate buffer solution having a pH value of 5 to 10 may be used, but it is preferred to carry out the reaction in a buffer solution of about pH 6 to 8. Furthermore, it is preferred to add a surfactant to the buffer solution for activating the enzyme or solubilization of the substrate. As the surfactant, a bile acid surfactant, a nonionic surfactant or the like may be used. Although the amount of the surfactant to be added is not particularly limited, it may be used in such an amount that its enzyme activating and substrate solubilizing effects can be obtained or the product can be obtained efficiently, so that it is preferred to add the agent preferably within the range of 0.01% to 1%. Also, an organic solvent may be added to the reaction solution. The amount of the organic solvent to be added is not particularly limited, with the proviso that it is such an amount that the enzyme is not inactivated and the product can be obtained efficiently.

The thus obtained sphingolipid or sphingolipid derivative can be confirmed by thin layer chromatography.

The sphingolipid obtained by the present invention can be isolated and purified by chromatography conventional for organic compounds.

According to the present invention, an SCDase having an extremely wide substrate specificity is provided.

Since the amino acid sequence and nucleotide sequence of an SCDase were revealed for the first time by the present invention, it became possible to provide a gene which encodes a polypeptide having SCDase activity. The present invention also provides a method for the industrially advantageous production of a polypeptide having SCDase activity by means of genetic engineering using the gene. As a result, purification of the enzyme can be made easily, because it is not necessary to add a ganglioside mixture to the medium for the induction production of the SCDase, and enzymes such as sphingomyelinase and the like are not simultaneously produced and fatty acids derived from the ganglioside mixture added to the medium are not formed.

Furthermore, since the SCDase gene was provided for the first time by the present invention, it rendered possible the provision of a recombinant polypeptide encoded by the gene, an antibody or a fragment thereof which specifically binds to the polypeptide and a probe or primer which specifically hybridizes to the SCDase gene.

Use of the enzyme of the present invention makes it possible to prepare lysosphingolipids from various sphingolipids.

These lysosphingolipids thus obtained can be further converted into sphingolipid derivatives by utilizing the free amino acids thereof by, for example, reintroducing a labeled fatty acid thereinto, directly labeling the same with a fluorescent substance or binding to a carbohydrate chain-free protein (e.g., albumin) in a conventional manner. These derivatives are useful as a substrate for assaying a carbohydrate-relating enzyme, as a ligand in affinity chromatography for purification, as an antigen against an anti-sphingolipid antibody or in a study for revealing the function of sphingolipids.

Further, the lysosphingolipid obtained using the enzyme of the present invention serves as a substrate or a reagent useful in the field of cell technology such as elucidation of intracellular metabolism and transport route of sphingolipids or function of sphingolipids in the cells.

Also, the process according to the present invention makes it possible to efficiently and economically produce lysosphingolipids in a large amount.

The present invention provides a method for producing sphingolipid derivatives, which is effected by modifying or substituting a long-chain fatty acid of the ceramide moiety as the common portion of a sphingolipid. Also, the use of the production method renders possible industrially advantageous production of arbitrary sphingolipids or sphingolipid derivatives. Since naturally occurring sphingolipids generally have diversity in terms of the chain length of the long-chain fatty acid, it was difficult to obtain sphingolipids having a uniform chain length of the long-chain fatty acid. However, sphingolipids whose long-chain fatty acid is unified can be obtained by the long-chain fatty acid substitution of the present invention. Also, since it is possible to prepare labeled sphingolipids by introducing a chromophore-forming substance, a fluorescent substance, biotin, a radioactive isotope or the like into the fatty acid moiety of a sphingolipid, the labeled sphingolipids can be applied to the elucidation of intracellular metabolism, transport pathway and the like of sphingolipids. Additionally, by the conversion of the ceramide moiety in the sphingolipid, for example, by the introduction of functional highly unsaturated fatty acid, such as eicosapentaenoic acid (EPA), docosahexaenoic acid (DHA) or the like, new sphingolipid derivatives having modified cell permeability, cell metabolism or biological activity can be created, which can be applied to medicines, cosmetics, cell technology and the like.

The production method of the present invention has rendered possible efficient and low-cost production of arbitrary sphingolipids or sphingolipid derivatives which are useful in medicines, sugar technology, cell technology and the like.

To further illustrate the present invention in greater detail, the following example will be given. However this example is intended to illustrate an example of the embodiment of the invention and is not to be construed to limit the scope of the same.

EXAMPLE 1

Isolation of SCDase

Pseudomonas sp. TK-4 (BP-5096) was inoculated to an inoculum size of 2% into a liquid medium, which contained 0.5% of peptone, 0.1% of yeast extract, 0.2% of NaCl and 0.1% of asialo GM1, and incubated therein at 30° C. for 48 hours. After the completion of the incubation, the culture medium was centrifuged at 6,000 rpm for 60 minutes. Thus the cells were eliminated and a culture supernatant was obtained. The subsequent procedures were all performed at 5° C. Ammonium sulfate was added to the culture supernatant to achieve 80% saturation. Then it was allowed to stand overnight and centrifuged at 6,000 rpm for 60 minutes. The precipitate thus obtained was collected and dissolved in a small amount of a 20 mM acetate buffer solution (pH 6.0) containing 0.2% of Lubrol. Next, it was dialyzed against the same buffer solution overnight. After the completion of the dialysis, the enzyme solution was subjected to gel filtration chromatography with the use of a Toyopearl HW-55F column (column size: 40×300 mm; manufactured by Tosoh Corporation). Elution was carried out using as an eluent a 20 mM acetate buffer solution (pH 6.0) containing 0.2% of Lubrol and 0.2 M of NaCl at a flow rate of 1 ml/min to collect fractions in 5 ml portions. Active fractions were collected and subjected to column chromatography using a DEAM column (column size: 2.3×150 mm; manufactured by J. T. Baker) which had been equilibrated with a 20 mM acetate buffer solution (pH 6.0) containing 0.2% of Lubrol. Elution was carried out using the same buffer solution at a flow rate of 2 ml/min to collect unadsorbed fractions. The resulting fractions were applied to a CM-5PW column (column size: 5×50 mm, manufactured by Tosoh Corporation) at a flow rate of 0.5 ml/min to collect fractions in 1.5 ml portions. The development was performed by linear gradation elution of from 0 to 1 M NaCl to collect active fractions which was subjected to gel filtration chromatography using a TSK-G300SW column (manufactured by Tosoh Corporation). Elution was carried out using a 20 mM acetate buffer solution (pH 6.0) containing 0.2% of Lubrol and 0.2 M of NaCl at a flow rate of 1.5 ml/min to collect fractions in 1.5 ml portions. Active fractions were collected and subjected to column chromatography of hydroxyapatite (column size: 1.4×70 mm) which had been equilibrated with a 2 mM phosphate buffer solution (pH 7.0) containing 0.2% of Lubrol. Elution was performed by linear gradient elution of from the starting buffer solution to a 400 mM phosphate buffer solution (pH 7.0). The active fractions were collected to give a purified enzyme. It was confirmed that this purified enzyme hydrolyzed asialo GM1 to form lysoasialo GM1 and a fatty acid.

EXAMPLE 2

Cloning of SCDase Structural Gene (1) Extraction and Purification of Genomic DNA An SCDase high production strain obtained by purifying an SCDase producing strain, Pseudomonas sp. TK-4 (FERM BP-5096), on a plate medium was named Pseudomonas sp. MF202, and Pseudomonas sp. MF202 was inoculated into 200 ml of LB medium (1% Bacto-trypton, 0.5% yeast extract, 0.5% NaCl) and cultured at 25° C. for 24 hours.

After completion of the culturing, the thus obtained culture broth was centrifuged to collect cells which were subsequently suspended in 10 ml of TE buffer (10 mM Tris-HCl, 1 mM EDTA, pH 8.0), and the resulting suspension was mixed with 0.2 ml of 50 mg/ml egg lysozyme and incubated at 30° C. for 15 minutes. This mixture was gently stirred by adding 2 ml of 10% SDS and then, when the solution became viscous, immediately mixed with 10 ml of saturated phenol in TE buffer and 1.5 ml of 5 M NaCl, and the mixture was gently stirred at room temperature for 1 hour. This mixture was centrifuged at 2,500 rpm for 10 minutes to recover the resulting upper layer. This mixture was mixed with the same volume of chloroform, stirred for 10 minutes and then subjected to 10 minutes of centrifugation at 1,500 rpm to recover the resulting upper layer. This mixture was again washed with the same volume of chloroform and then centrifuged (hereinafter, this process is referred to as "phenol-chloroform treatment").

The same volume of isopropyl alcohol was slowly added to the thus recovered upper layer, and the DNA molecules thus precipitated at the interface were rolled round a Pasteur pipette and dissolved in 10 ml of TE buffer. To this mixture was added 20 µl of RNase A solution (dissolved in a solution of 10 mM Tris-HCl and 15 mM NaCl, pH 7.5, to a concentration of 10 mg/ml and heated at 100° C. for 10 minutes to deactivate DNase), subsequently incubating the solution at 50° C. for 1 hour.

To this mixture were further added 100 µl of protease K solution (a solution prepared by dissolving proteinase K in distilled water to a concentration of 20 mg/ml), 200 µl of 5 M NaCl and 400 µl of 10% SDS, subsequently incubating the mixture at 37° C. for 1 hour. After completion of the reaction, this mixture was returned to room temperature and mixed with the same volume of phenol-saturated TE buffer to carry out phenol-chloroform treatment. This step was repeated twice, and the resulting water layer was mixed with the same volume of isopropyl alcohol and ⅒ volume of 3 M sodium acetate and cooled at −20° C. for 1 hour. Thereafter, this mixture was centrifuged at 10,000 rpm for 10 minutes, the resulting precipitate was rinsed with 70% ethanol and dissolved in an appropriate amount of TE buffer, and the thus obtained solution was used as a genomic DNA solution.

Concentration of the thus obtained genomic DNA in this manner was calculated to be about 600 µg based on its absorbance.

(2) Determination of SCDase Partial Amino Acid Sequence

The SCDase purified by the method described in *Journal of Biological Chemistry*, 270:24370–24374 (1995) was further purified by reverse HPLC.

Cosmosil™ 5C4-AR-300 (manufactured by Nakalai Tesque) was used as the column, and solution A (0.1% trifluoroacetic acid (TFA)) and solution B (0.1% TFA containing 80% acetonitrile) were used as the eluting system. The elution was carried out by increasing the ratio of the solution B linearly from 0 to 100% over a 50 minute period at a flow rate of 0.5 ml/min.

The thus purified SCDase was directly subjected to an amino acid sequence analysis by the gas phase Edman degradation method in the conventional way, thereby determining an N-terminal amino acid sequence N (SEQ ID NO:3).

Next, the enzyme protein was digested with a lysyl endopeptidase, and peptide fragments were separated and purified from the thus obtained digest by HPLC.

µBondasphare C8 (manufactured by Waters) was used as the column, and solution A (0.1% TFA) and solution B (0.1% TFA containing 80% acetonitrile) were used as the eluting system. The elution was carried out by increasing the ratio of the solution B linearly from 0 to 100% over a 50 minute period at a flow rate of 0.5 ml/min.

By carrying out amino acid sequence analysis on each peptide fraction, partial amino acid sequences N-8 (SEQ ID NO:6), N-32 (SEQ ID NO:8) and N-34 (SEQ ID NO:9) were determined.

(3) Cloning of DNA Fragment Containing SCDase Gene

On the basis of the information on partial amino acid sequences obtained in the above step (2), oligonucleotide primers were designed and synthesized for PCR. That is, an oligonucleotide primer-1 (SEQ ID NO:4) and an oligonucleotide primer-2 (SEQ ID NO:5), designed from the N-terminal amino acid sequence N (SEQ ID NO:3), and an oligonucleotide primer-3 (SEQ ID NO:7) designed from the partial amino acid sequence N-8 (SEQ ID NO:6) were synthesized.

In this case, two different oligonucleotide primers 1 and 2 were designed for leucine because of the presence of many codons for this amino acid. Additionally, in order to facilitate determination of the nucleotide sequence of the amplified product, each primer was designed such that an EcoRI site was added to its 5'-end side.

PCR was carried out using GeneAmp™ Reagent Kit (manufactured by Perkin-Elmer). A total of 30 cycles of the PCR was carried out, with one cycle being 94° C. for 0.5 minute, 50° C. for 1 minute and 72° C. for 1 minute.

By one PCR using 1 $\mu$g of the genomic DNA of Pseudomonas sp. TK-4 obtained in the above-described step (1) as the template and using a combination of the primer-1 (SEQ ID NO:4) with the primer-3 (SEQ ID NO:7), a specific band which seemed to be an amplified DNA fragment (about 550 bp) was detected by agarose gel electrophoresis.

The PCR product was digested with a restriction enzyme EcoRI (manufactured by Takara Shuzo) and recovered from an agarose gel using Sephaglas™ BandPrep Kit (manufactured by Pharmacia Biotech).

Next, an alkaline phosphatase-treated plasmid pGEM-3Z (manufactured by Promega) was digested with EcoRI and then ligated with the thus recovered PCR product using T4 DNA ligase (manufactured by Life Technologies). The thus obtained plasmid was named pGEM PCR.

Nucleotide sequence of the amplified DNA fragment was determined by the dideoxy chain termination method. The thus determined nucleotide sequence of the PCR product is represented by SEQ ID NO:10 in the Sequence Listing. In this case, a primer-derived EcoRI site is added to the 5'- and 3'-sides of the nucleotide sequence.

As the result, it was successful in obtaining a portion of the SCDase gene of interest, because, in addition to the sequences of primer-1 and primer-3, a sequence corresponding to the partial amino acid sequence of SCDase was found in the thus determined nucleotide sequence.

(4) Cloning of SCDase Gene

Screening of the genomic DNA prepared in the above-described step (1) was carried out using the DNA fragment (SEQ ID NO:10) obtained in the above step (3) as a probe.

Firstly, 10 $\mu$g of the genomic DNA prepared in the step (1) was completely digested with 100 units of each of restriction enzymes EcoRI, BamHI, SmaI, HindIII, PstI, SacI and KpnI (all manufactured by Takara Shuzo), each at 37° C. for 16 hours. A 10 $\mu$g portion of each of the DNA fragments obtained from the reaction solution by phenol extraction was subjected to 0.7% agarose gel electrophoresis. After the electrophoresis, the DNA fragments were transferred on a nylon membrane (Hybond-N$^+$, manufactured by Amersham) by the Southern blotting method (*Gene Research Methods II*, 218–221, Tokyo Kagaku Dojin).

A 0.1 $\mu$g portion of the DNA fragment (SEQ ID NO:10) obtained in the above step (3) was labeled with $^{32}$P using Ready-To-Go™ DNA Labeling Kits (manufactured by Pharmacia Biotech) in accordance with the protocol attached to the kits and used as the probe for hybridization.

The filter membrane prepared in the above was subjected to 1 hour or more of pre-hybridization at 65° C. in a hybridization solution containing 0.5 M piperazine-1,4-bis (2-ethanesulfonic acid) monosodium salt (Na-PIPES, pH 7.0), 7% SDS and 5 mM EDTA and then the labeled probe was added thereto to a final concentration of 6 pmol/ml to carry out overnight hybridization at 65° C.

Next, the membrane was washed three times, each at 65° C. for 15 minutes, in a washing solution (40 mM sodium phosphate buffer containing 1% SDS) which had been incubated at 65° C. in advance. After removal of excess moisture, this mixture was exposed to light for 20 minutes on a imaging plate of Imaging Analyzer BAS 1000 (manufactured by Fiji Photo Film) to detect bands.

As the results, bands capable of hybridizing to the used probe were found at positions of about 11.0 kb in the EcoRI digest, about 5.7 kb in the BamHI, about 3.5 kb in the HindIII digest, about 0.7 kb in the PstI digest, about 11.0 kb in the SacI digest and about 10.3 kb in the KpnI digest.

For the sake of easy handling, the following experiments were carried out using the HindIII digest of about 3.5 kb.

A 1 cm length of a gel position, which corresponded to the band found by the above hybridization test after the above-described 0.7% agarose gel electrophoresis of 10 $\mu$g genomic DNA digested with HindIII, was cut out into 2 mm portions. These portions were named fractions 1, 2, 3, 4 and 5 starting from the shortest migration distance.

Each of these gel fractions was extracted and purified by a phenol freeze-thawing method, and each of the DNA fragments thus recovered was again subjected to agarose gel electrophoresis and then to hybridization using the above-described probe.

As the results, the strongest signal was observed in the fraction 2.

Consequently, the HindIII-digested DNA fragment of fraction 2 was inserted into the HindIII site of pBluescript™ II SK (manufactured by Stratagene).

*Escherichia coli* JM109 was transformed with this plasmid, cultured overnight and then inoculated into 10 round Petri dishes of 8.5 cm in diameter, each containing LB agar medium supplemented with 100 $\mu$g/ml of ampicillin. From 200 to 1,000 per dish of colonies thus formed, 65 colonies were selected and transferred onto a nylon membrane (Hybond-N$^+$, manufactured by Amersham) placed on the same plate medium. After 16 hours of culturing at 37° C., the nylon membrane was treated (denaturation) for 5 minutes on a filter paper impregnated with a solution of 0.5 M NaOH and 1.5 M NaCl, treated (neutralization) for 5 minutes on a filter paper impregnated with a solution of 0.5 M Tris-HCl buffer (pH 7.5) and 3 M NaCl and then rinsed with 2×SSC. When this nylon membrane was subjected to hybridization using the DNA fragment (SEQ ID NO:10) obtained in the above-described step (3) as a probe under the same conditions, 10 positive signals were obtained. Plasmid DNA was extracted from each colony which showed a positive signal, thermally denatured at 100° C. for 3 minutes and plotted on the nylon membrane (Hybond-N$^+$, manufactured by Amersham), and then dot hybridization was carried out using the above-described probe (SEQ ID NO:10) to find that 9 of the plasmid DNA samples showed a positive signal.

One of these samples was named pSK 33 and used in the following experiments.

By digesting pSK 33 with several restriction enzymes, its digestion pattern was analyzed by electrophoresis. As the results, the presence of a total of 10 restriction enzyme sites, including SmaI, PstI and SalI sites, was confirmed.

Also, in order to determine nucleotide sequence of the above-described HindIII digest, various deletion mutants were prepared in the conventional way using the XhoI and KpnI sites present in the multicloning site of pSK 33, using restriction enzymes XhoI and KpnI (manufactured by Takara Shuzo), Exonuclease III (manufactured by Nippon Gene) and Mung Bean Nuclease (manufactured by Nippon Gene).

When nucleotide sequences of the thus obtained deletion mutants were determined by the dideoxy chain termination method, the presence of the nucleotide sequence of the PCR product (SEQ ID NO:10) was revealed, and then the presence of nucleotide sequences coding for the N-terminal amino acid sequence N (SEQ ID NO:3) and partial amino acid sequences N-8 (SEQ ID NO:6), N-32 (SEQ ID NO:7) and N-34 (SEQ ID NO:8).

Additionally, an open reading frame (ORF) was found in the HindIII insertion fragment of pSK 33. All sequences corresponding to the SCDase amino acid sequences analyzed and determined in the above-described step (2) were found in this ORF.

On the basis of the above results, the complete nucleotide sequence and primary structure of the SCDase gene were determined.

The complete nucleotide sequence of the ORF in the SCDase is represented by SEQ ID NO:11 in the Sequence Listing, and the complete amino acid sequence encoded by this nucleotide sequence is represented by SEQ ID NO:12 in the Sequence Listing. Furthermore, a series of the amino acid residues of position 1 to position 25 in the amino acid sequence represented by SEQ ID NO:12 in the Sequence Listing seemed to be a signal-like sequence on the basis of the information on the N-terminal amino acid sequence N (SEQ ID NO:3) of SCDase obtained in the above step (2).

Figure 8:
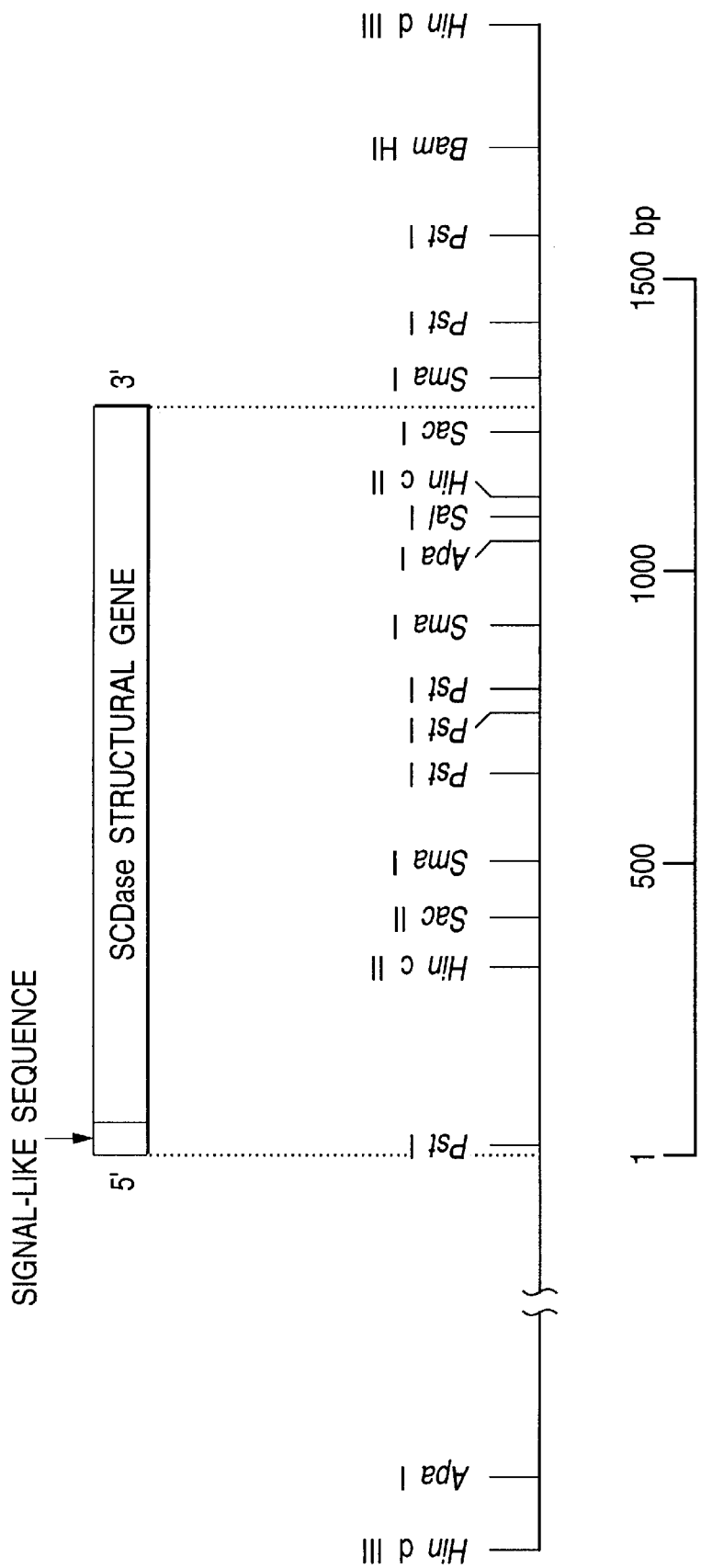
FIG. 8 is a graph which shows a correlation between the restriction enzyme map of insertion HindIII fragment of pSK 33 and the SCDase gene.

The results of this are shown in FIG. 8. That is, FIG. 8 is a graph which shows a correlation between the restriction enzyme map of an insertion HindIII fragment of pSK 33 and the position of the SCDase gene.

In FIG. 8, dotted lines indicate translation initiation point and translation end point of SCDase, and the coding region of the SCDase gene is shown thereon.

Moreover, the nucleotide sequence of the gene encoding the SCDase, excluding the signal sequence, is represented by SEQ ID NO:2 in the Sequence Listing, and the amino acid sequence which could be encoded by this sequence is represented by SEQ ID NO:1 in the Sequence Listing.

The thus obtained plasmid pSK 33 containing the full length of the SCDase gene was introduced into *Escherichia coli* JM109, and the resulting strain, named *Escherichia coli* JM109/pSK 33, has been deposited in the above-identified National Institute of Bioscience and Human Technology, Agency of Industrial Science and Technology, and had been assigned the designation as FERM P-16723.

EXAMPLE 3

Construction of Plasmid Capable of Expressing SCDase Polypeptide (1) Construction of Plasmid Containing Full Length SCDase Gene In order to construct a plasmid capable of expressing an SCDase polypeptide, pSK 33 was digested with a restriction enzyme PstI (manufactured by Takara Shuzo), the resulting DNA fragment containing a gene coding for a C-terminal side moiety of the SCDase was purified by 1% agarose gel electrophoresis and sub-cloned into the PstI site of pBluescript™ II SK (manufactured by Stratagene), and the thus obtained plasmid was named pSK P4.

The thus obtained pSK P4 was digested with a restriction enzyme ApaI (manufactured by Takara Shuzo), and a DNA fragment containing a gene coding for a C-terminal side moiety of the SCDase was extracted and purified. This DNA fragment was further digested with a restriction enzyme PstI (manufactured by Takara Shuzo), and a DNA fragment of about 260 bp containing a gene coding for a C-terminal side moiety of the SCDase was extracted and purified by 1% agarose gel electrophoresis and used as fragment 1.

Next, among the deletion mutants of pSK 33 prepared in Example 2-(4) for use in the determination of the HindIII digest, a plasmid having a DNA fragment containing a gene in which a part of the N-terminal side of SCDase is deleted was selected and named pSK D38.

The thus selected pSK D38 was double-digested with restriction enzymes ApaI (manufactured by Takara Shuzo) and SacII (manufactured by Takara Shuzo), and a DNA fragment of about 750 bp containing a gene coding for a central moiety of the SCDase was extracted and purified by 1% agarose gel electrophoresis and used as fragment 2.

Next, pGEM PCR prepared in Example 2-(3) was digested with a restriction enzyme EcoRI (manufactured by Takara Shuzo), and the EcoRI digestion fragment was purified by phenol treatment. The thus purified EcoRI digestion fragment was further digested with a restriction enzyme SacII (manufactured by Takara Shuzo), and a DNA fragment of about 330 bp containing a gene coding for an N-terminal side moiety of the SCDase was extracted and purified by 1% agarose gel electrophoresis and used as fragment 3.

A plasmid pTV118N (manufactured by Takara Shuzo) was double-digested with restriction enzymes EcoRI (manufactured by Takara Shuzo) and PstI (manufactured by Takara Shuzo), and an EcoRI-PstI digest of pTV118N was extracted and purified by 1% agarose gel electrophoresis.

The thus purified EcoRI-PstI digest of pTV118N was mixed with the above-described fragments 1, 2 and 3 and ligated using DNA Ligation Kit (manufactured by Takara Shuzo). A 10 µl portion of the resulting ligation reaction solution was used for the transformation of *Escherichia coli* JM109. After the transformation, the thus transformed cells were cultured overnight and spread on LB agar medium containing 100 µg/ml of ampicillin, a total of 16 colonies thus formed showing blue color were selected arbitrarily and then plasmid DNA was extracted from each colony. The thus obtained plasmid was digested with various restriction enzymes to confirm the inserted fragments.

As the results, a plasmid into which a DNA fragment containing a gene coding for the SCDase had been correctly inserted, namely a plasmid into which the insertion fragments had been correctly inserted in order of fragments 3, 2 and 1 counting from the 5'-end side, was selected and named pTV EcoRI/PstI.

Moreover, the SCDase activity was found in a crude extract prepared from *Escherichia coli* JM109 which had been transformed with pTV EcoRI/PstI.

EXAMPLE 4

Production of Lysosphingolipid (1) Production of Lysoasialo GM1

Asialo GM1 was used as a sphingolipid. It was prepared from bovine brain in accordance with the method described in Methods in Enzymology, 83:139–191 (1982). The purified enzyme obtained in Example 1 (40 mU) was added to 200 µl of 25 mM acetate buffer (pH 6.0) containing 2.5 mg/ml of asialo GM1 and 0.8% Triton X-100 and the resulting mixture was incubated at 37° C. for 3 days to perform the reaction. After the completion of the reaction, partition was carried out by adding chloroform/methanol (2/1 by volume) in a 5-fold amount of the reaction mixture. The upper layer is recovered and evaporated to dryness. The resulting residue was dissolved in 500 µl of chloroform/methanol/water (3/48/47 by volume) and subjected to ODS reverse phase column chromatography to thereby separate the reaction product and unreacted sphingolipid (asialo GM1). An ODS-80T column (4.6×75 mm, Tosoh Corporation) was used therefor. The flow rate was set to 1 ml/min and fractions were collected in 1.5 ml portions. Elution was carried out using chloroform/methanol/water (5/4/1 by volume). Eluates were monitored by HPTLC analysis. HPTLC was carried out using chloroform/methanol/10% acetic acid (5/4/1 by volume) as a developing solvent using the orcinol-sulfuric acid method for color development. For exclusive detection of a lysosphingolipid, the ninhydrin method was used.

Fractions containing lysoasialo GM1 were collected to serve as a purified product and subjected to FAB-MS analysis (matrix: triethanolamine). The results are shown in FIG. 5. The ordinate and abscissa stand for relative intensity and mass-to-charge ratio (M/Z), respectively. Signal 987 which corresponds to molecular weight 988 of lysoasialo GM1 was observed as the strongest signal. FIG. 5 also shows signal 825 indicating that Gal was liberated from the nonreducing end of the carbohydrate chain of lysoasialo GM1 and signal 622 indicating that N-acetylgalactosamine (GalNAc) was further liberated therefrom.

The purified product is positive in the ninhydrin reaction. When the purified product was treated with endoglycoceramidase, the carbohydrate chain moiety of asialo GM1 was formed. The resulting carbohydrate chain moiety was negative in the ninhydrin reaction.

From these results, the purified reaction product was found to be lysoasialo GM1.

(2) Production of Lysosphingomyelin

The same procedure as in Example 4 (1) was repeated using sphingomyelin (manufactured by Matreya) as a sphingolipid except for using silica gel 60 column in place of ODS-BOT column under the same conditions as in the case of using ODS-80T column and performing color development by the Coomassie Brilliant Blue method in place of the orcinol method.

Figure 6:
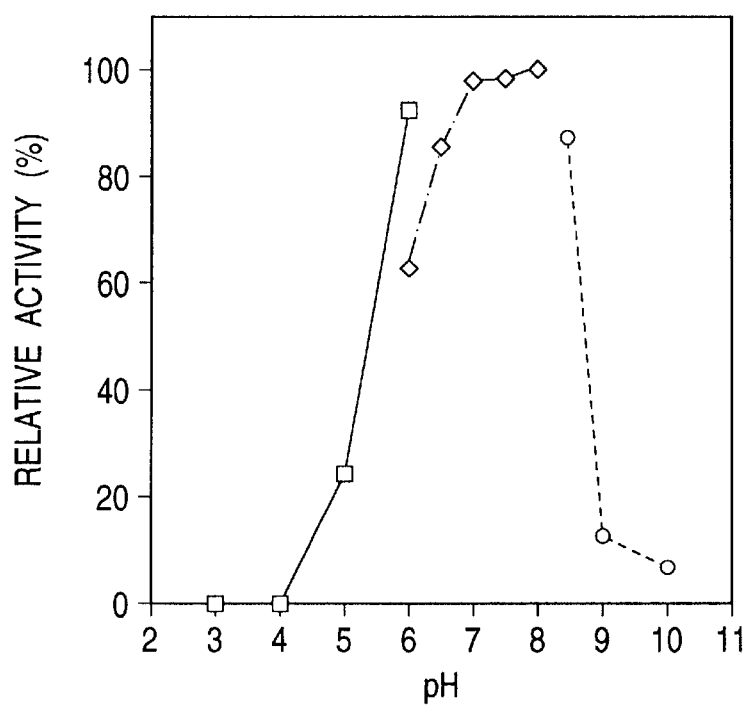
FIG. 6 is an FAB-mass spectrum of the lysosphingomyelin obtained by digesting sphingomyelin with the use of the SCDase obtained by the present invention.

The results of FAB-MS analysis of the reaction product are shown in FIG. 6. The ordinate and abscissa stand for relative intensity and mass-to-charge ratio (M/Z), respectively. FIG. 6 is a magnification in the range from 400 to 550 (M/Z).

As shown in FIG. 6, the strongest signal was signal 467 [(M+H$^+$)] corresponding to the molecular weight 466 of lysosphingomyelin.

EXAMPLE 5

Synthesis of Lysosphingolipid Derivatives (1) Introduction of Single Chain Fatty Acid to Lysosphingolipid A fatty acid was introduced to a lysosphingolipid by reacting synthesized fatty acid chloride with a lysosphingolipid (reacylation). Lyso-GM1 was prepared in the same manner as described in Example 4 (1) and used as a lysosphingolipid. As a fatty acid, molecular species of C2:0, C14:0, C16:0, C18:0, C22:0 and C24:0 were used. Two to three molar equivalents of a fatty acid to lyso-GM1 was put into a small flask and 5 to 10 ml of thionyl chloride was added thereto. Attaching a condenser, the flask was heated at about 80° C. in water bath under reflux. In this instance, the reflux condenser was equipped with a glass tube packed with calcium chloride at its tip for blocking the outside air. After the completion of the reaction, thionyl chloride was removed under nitrogen gas stream in a draft and the flask was allowed to stand in a desiccator with potassium hydroxide for 1 to 2 hours. With confirming no smell of thionyl chloride, diethyl ether was added to the flask to dissolve the reaction product contained therein. Further, 1 µmol of lyso-GM1 dissolved in 1 ml of 0.3 M sodium hydrogencarbonate solution was added thereto followed by stirring for 2 to 3 hours. The reaction was monitored by TLC. After the completion of the reaction, the reaction mixture was dialyzed against ultrapure water to obtain reacylated GM1. According to this method, any fatty acid could be introduced to lyso-GM1 in a yield of about 90% irrespective of the length of the carbon chain of the fatty acid.

(2) Synthesis of Fluorescence-labeled Neosphingolipid

Fluorescence-labeled sphingolipid derivatives (fluorescence-labeled neosphingolipids) were synthesized by fluorescence-labeling an amino group of the sphingosine moiety of a lysosphingolipid. Lyso-GM1 was prepared in the same manner as described in Example 4 (1) and used as a lysosphingolipid.

For labeling with dansyl chloride, lyso-GM1 (1 µmol) was dissolved in 1 ml of 0.2 M sodium hydrogencarbonate solution and an equivalent volume of 0.25% dansyl chloride in acetone was added thereto. The resulting mixture was allowed to stand in the dark at 37° C. for 1 hour and dialyzed against ultrapure water.

On the other hand, in labeling with NBD-F, Lyso-GM1 (0.5 nmol) was dissolved in 500 µl of 0.1 M borate buffer (pH 8.0), 500 µl of 20 mM NBD-F/ethanol solution was added thereto and the resulting mixture was incubated in water bath at 60° C. for 1 minute. Immediately thereafter, the reaction mixture was cooled in ice and dialyzed against ultrapure water at 4° C. for about 2 hours.

In both cases, it was necessary to carry out the reaction in the dark.

The thus synthesized fluorescence-labeled neosphingolipid was assayed by TLC using chloroform/methanol/10% acetic acid (5/4/1 by volume) as a developing solvent. The yield of dansylated GM1 (Dansyl-II$^3$NeuAcα-Gg4-sphingosine) was almost 100%, while that of NBD-GM1 (NBD-II$^3$NeuAcα-Gg4-sphingosine) was 70–80%.

EXAMPLE 6

Production of lyso-GM1 by Pseudomonas sp. TK-4

A 60 ml portion of PY medium (polypeptone 0.5%, yeast extract 0.1%, sodium chloride 0.2%; pH 7.2) containing 30 mg of ganglioside GM1 (manufactured by Iatron) and 0.1% of 2,6-O-dimethyl-β-cyclodextrin was sterilized and inoculated with the strain which had been incubated overnight in a slant medium containing 0.1% of crude bovine brain ganglioside prepared in accordance with the method described in Methods in *Enzymology*, 14:660–664 (1969). Then, the strain was incubated therein under shaking at 25° C. for 3 days.

Then the cells were eliminated by centrifuging the culture medium and thus the culture supernatant was obtained. When the culture supernatant was analyzed by thin layer chromatography, it was found that the ganglioside GM1 was completely converted into lyso-GM1.

This culture supernatant was added to a Sep-Pak C18 column (manufactured by Waters) and the unadsorbed fraction was washed away with water. Next, methanol in the same volume as the column volume was poured into the column followed by elution with chloroform/methanol=1/2 (by volume) to obtain lyso-GM1.

Subsequently, the lyso-GM1 thus obtained was evaporated to dryness and dissolved in chloroform/methanol/ water=60/30/5 (by volume). Further, it was subjected to high performance liquid chromatography by using an Aquasil SS-1251 column (4.6×250 mm, manufactured by Senshu Kagaku) and eluted with chloroform/methanol/water (60/30/5 by volume) at a flow rate of 1.5 ml/min to purify the lyso-GM1. Thus 18 mg of the purified lyso-GM1 could be obtained.

EXAMPLE 7

Conversion of Various Glycosphingolipids into lyso-forms by Pseudomonas sp. TK-4

PY medium (polypeptone 0.5%, yeast extract 0.1%, sodium chloride 0.2%; pH 7.2) containing 0.1% of 2,6-O-dimethyl-β-cyclodextrin was sterilized in an autoclave and filter-sterilized aqueous solutions of various glycosphingolipids [i.e., GM1, GM2 (manufactured by Matreya), GM3 (manufactured by Iatron), GD1a (manufactured by Iatron), GD1b (manufactured by Iatron), GD3 (manufactured by Iatron), GT1b (manufactured by Biocarb), sulfatide (manufactured by Matreya): each 0.5 mg/ml, Gb4 (manufactured by Iatron): 0.1 mg/ml] were added thereto. Then each medium was inoculated with Pseudomonas sp. TK-4, which had been incubated overnight in a slant medium containing 0.1% of crude bovine brain ganglioside, followed by incubation at 25° C. under shaking for 3 days.

Then the cells were eliminated by centrifuging the culture medium to obtain the culture supernatant which was then analyzed by thin layer chromatography. The results are shown in Table 3 below.

TABLE 3

| Ganglioside | Digestion ratio (%) |
| --- | --- |
| GM1 | 100 |
| GM2 | 100 |
| GM3 | 100 |
| GD1a | 100 |
| GD1b | 100 |
| GD3 | 100 |
| GT1b | 100 |
| Gb4 | 56 |
| Sulfatide | 100 |

EXAMPLE 8

Production of Sphingosylphosphorylcholine (Lysosphingo-myelin) by Shewanella alga NS-589

Shewanella alga NS-589 was inoculated into 200 ml of a synthetic medium (dipotassium hydrogenphosphate 0.05%, ammonium chloride 0.05%, sphingomyelin 0.1%, sodium taurodeoxycholate 0.1%, sodium chloride 2%, 2,6-O-dimethyl-β-cyclodextrin 0.1%; pH 7.4) and incubated therein at 30° C. under shaking for 2 days.

Then the cells were eliminated by centrifuging the culture medium to obtain the culture supernatant which was then analyzed by thin layer chromatography. As a result, it was found that 80% of the sphingomyelin had been converted into sphingosylphosphorylcholine. This culture medium was added to a $C_{18}$ reversed phase column [Preoperative $C_{18}$ 125A (manufactured by Millipore), packing: 30 g, column diameter: 30 mm, open column]. After desalting and washing with 300 ml of water, the column was eluted with 300 ml of methanol and 300 ml of chloroform/methanol=1/1 (by volume). Then the sphingosylphosphorylcholine was eluted into the methanol fraction. After removing the solvent in the sphingosylphosphorylcholine fraction with a rotary evaporator, the residue was added to a silica gel 60 column (manufactured by Merck) and fractionated with chloroform/methanol/water=5/4/1 (by volume). Further, the solvent in the sphingosylphosphorylcholine fraction thus obtained was removed with a rotary evaporator and the residue was freeze-dried. Thus 47.6 mg of purified sphingosylphosphorylcholine could be obtained.

This purified sphingosylphosphorylcholine was developed by thin layer chromatography and stained with Coomassie Brilliant Blue. As a result, a single band was obtained. After digesting with sphingomyelinase (manufactured by Sigma) derived from Staphylococcus aureus, it was analyzed by thin layer chromatography. Thus, it was confirmed that sphingosine had been liberated. Further, it was analyzed by FAB-mass spectrometry and thus ion peaks $(M+H)^+$ at 465 and $(M+Na)^+$ at 487 were confirmed.

Based on these results, it has been clarified that sphingosylphosphorylcholine with a high purity can be obtained by this process.

EXAMPLE 9

Examination on Medium Composition in the Production of Sphingosylphosphorylcholine (Lysosphigomyelin) by Shewanella alga NS-589

The following media were prepared. First, sodium chloride concentrations of PY medium (polypeptone 0.5%, yeast extract 0.1%, sodium chloride 1%, sphingomyelin 0.1%, sodium taurodeoxycholate 0.1%; pH 7.2) and a synthetic medium (dipotassium hydrogenphosphate 0.05%, ammonium chloride 0.05%, sphingomyelin 0.1%, sodium taurodeoxycholate 0.1%; pH 7.4) were each regulated to 0%, 0.5%, 1%, 2% and 3%. To the synthetic medium, was added 0.05% of yeast extract and the sodium chloride concentration was regulated to 0%, 0.5%, 1%, 2% and 3%. To the synthetic medium containing 1% of sodium chloride was added 0.1% of glucose. Furthermore, a series of these media containing 0.1% of 2,6–O-dimethyl-β-cyclodextrin and another series thereof free from 2,6-O-dimethyl-β-cyclodextrin were prepared. Each medium was inoculated with Shewanella alga NS-589 which was then incubated therein under shaking at 25° C. for 3 days. The culture supernatant thus obtained was developed by thin layer chromatography and the formation of sphingosylphosphorylcholine was analyzed.

The sphingosylphosphorylcholine was stained with Coomassie Brilliant Blue and then determined by the densitogram at 600 nm with the use of a TLC Chromatoscanner CS9000 (manufactured by Shimadzu). FIG. 9 shows the results. Namely, FIG. 9 shows the amounts of the sphingosylphosphorylcholine product expressed in peak area at 600 nm wherein the ordinate refers to peak area while the abscissa refers to NaCl concentration (%).

Figure 9:
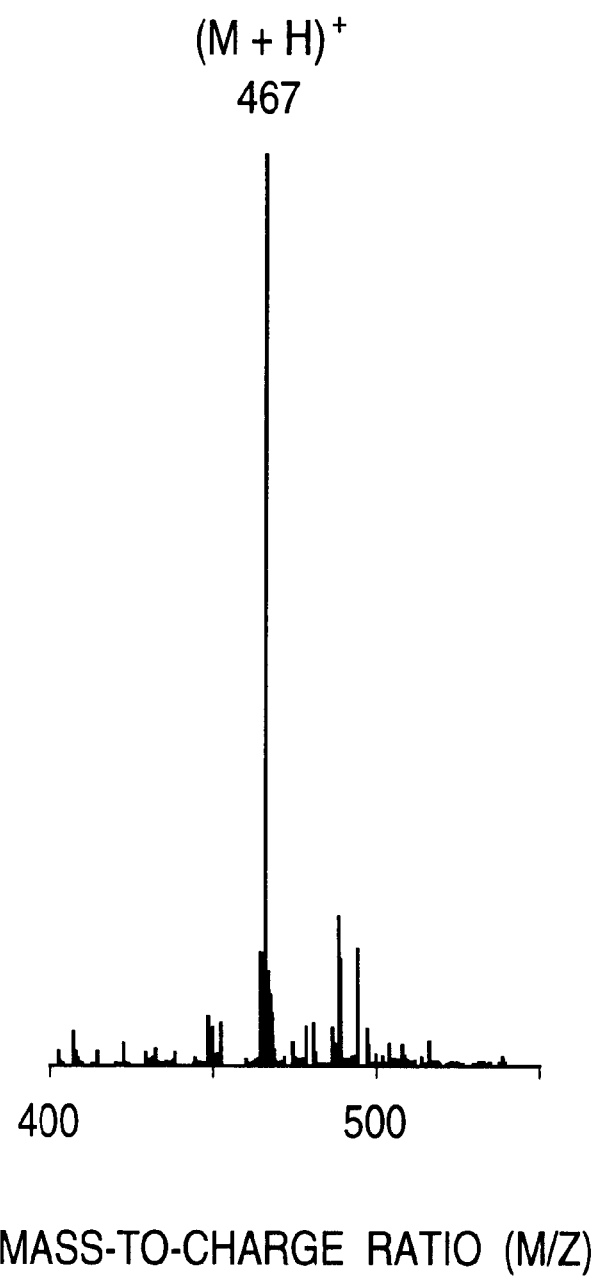
FIG. 9 is a graph which shows the temperature stability of the SCDase produced by the bacterium of the genus Shewanella of the present invention.

As FIG. 9 shows, no sphingosylphosphorylcholine was formed in the PY medium and the media free from sodium chloride. The maximum yield of sphingosylphosphorylcholine was achieved in the synthetic medium containing 2% of sodium chloride and 0.1% of 2,6-O-dimethyl-β-cyclodextrin.

EXAMPLE 10

Examination on Incubation Temperature in the Production of Sphingosylphosphorylcholine (Lysosphingomyelin) by Shewanella alga NS-589

Figure 10:
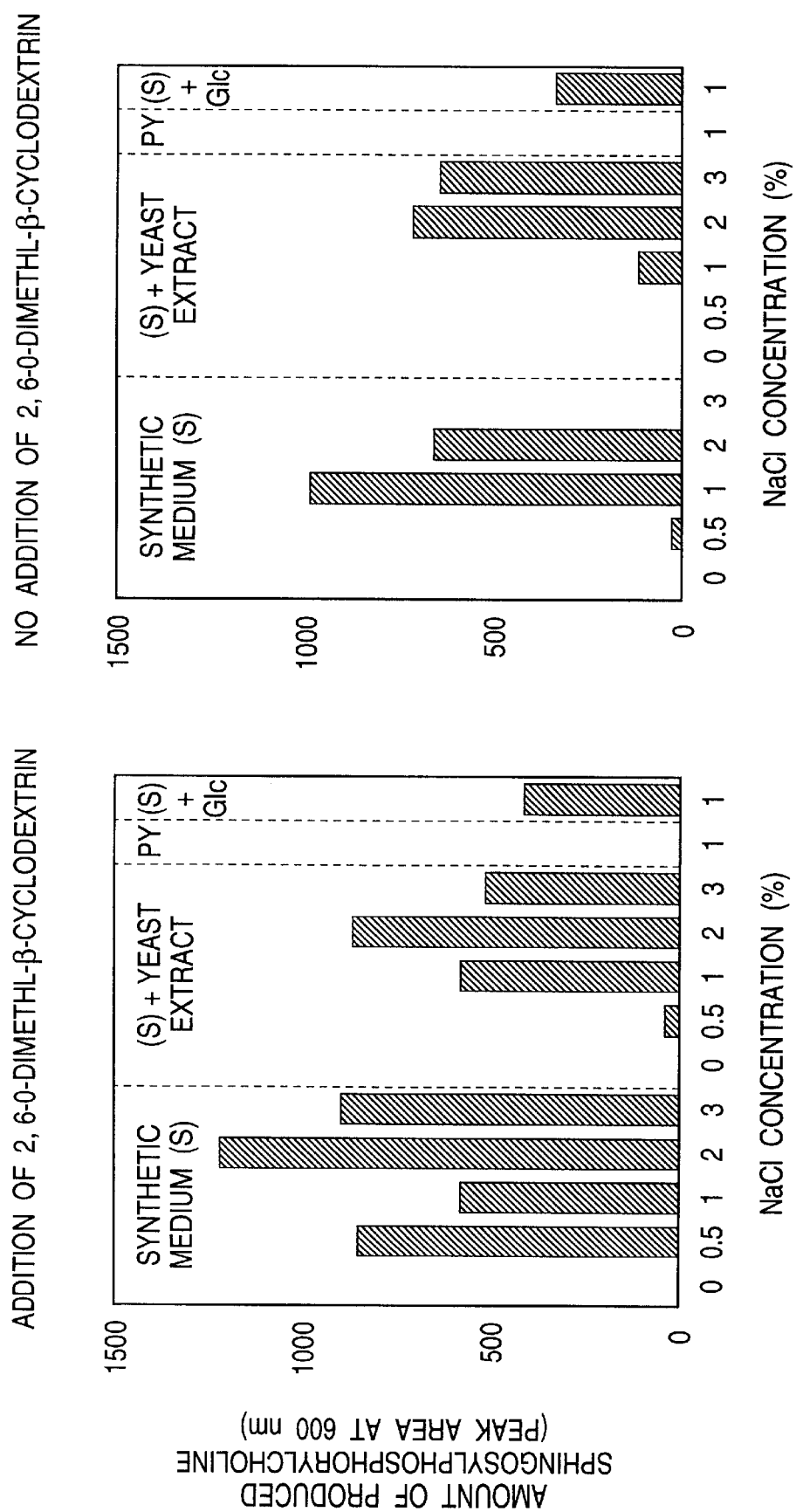
FIG. 10 is a graph which shows the examination on the medium composition in the production of sphingosylphosphorylcholine by the bacterium of the genus Shewanella of the present invention.

Shewanella alga NS-589 was incubated in a synthetic medium (dipotassium hydrogenphosphate 0.05%, ammonium chloride 0.05%, sphingomyelin 0.1%, sodium taurodeoxycholate 0.1%, sodium chloride 2%, 2,6-O-dimethyl-β-cyclodextrin 0.1%; pH 7.4) at 25° C., 30° C. and 37° C. for 3 days. Then sphingosylphosphorylcholine formed in each case was determined by densitogram at 600 nm with the use of a TLC Chromatoscanner CS9000 (manufactured by Shimadzu). FIG. 10 shows the results. Namely, FIG. 10 shows the amounts of the sphingosylphosphorylcholine product expressed in peak area at 600 nm wherein the ordinate refers to peak area while the abscissa refers to temperature (° C.). As FIG. 10 shows, the optimum temperature for the production of sphingosylphosphorylcholine is 30° C.

EXAMPLE 11

Figure 11:
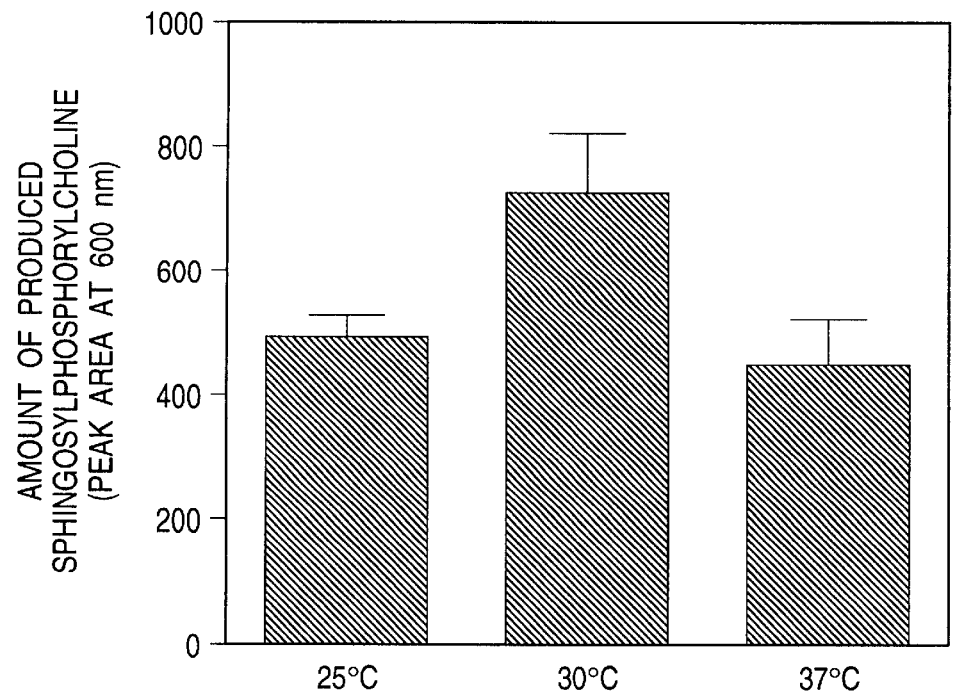
FIG. 11 is a graph which shows the examination on the incubation temperature in the production of sphingosylphosphorylcholine by the bacterium of the genus Shewanella of the present invention.
Figure 12:
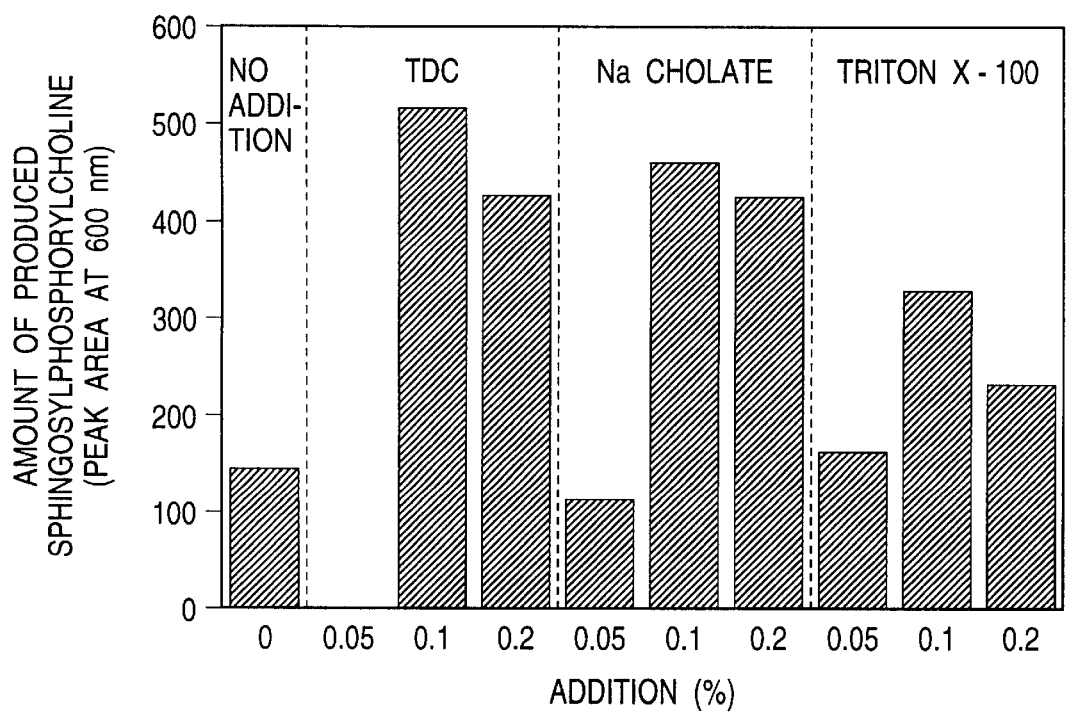
FIG. 12 is a graph which shows the examination on the addition of surfactants in the production of sphingosylphosphorylcholine by the bacterium of the genus Shewanella of the present invention.

Examination on the Addition of Surfactants in the Production of Sphingosylphosphorylcholine (Lysosphingomyelin) by *Shewanella alga* NS-589:

*Shewanella alga* NS-589 was incubated in a synthetic medium (dipotassium hydrogenphosphate 0.05%, ammonium chloride 0.05%, sphingomyelin 0.1%, sodium chloride 2%, 2,6-O-dimethyl-β-cyclodextrin 0.1%; pH 7.4) in the presence of surfactants at various concentrations at 30° C. for 3 days. Then sphingosylphosphorylcholine formed in each case was determined by densitogram at 600 nm with the use of a TLC Chromatoscanner CS9000 (manufactured by Shimadzu). FIG. 11 shows the results. As the surfactants, use was made of sodium taurodeoxycholate (TDC), sodium cholate (Na cholate) and Triton X-100 each at concentrations of 0.05%, 0.1% and 0.2% in the medium. In FIG. 11, the ordinate refers to peak area while the abscissa refers to the concentration of surfactant (%). As FIG. 11 shows, sodium taurodeoxycholate is the most suitable surfactant for the production of sphingosylphosphorylcholine.

EXAMPLE 12

Synthesis of Galactoceramide by SCDase

A 50 μl portion of 50 mM acetate buffer (pH 6.0) containing 5 nmol galactosylsphingosine (manufactured by Sigma), 5 nmol [1-$^{14}$C] stearic acid (manufactured by Amersham), 0.8% Triton X-100 and 150 μU SCDase derived from the genus Pseudomonas [*Journal of Biological Chemistry*, 270:24370–24374 (1995), European Patent 707063 A1 (1996)] was allowed to react overnight at 37° C.

The reaction solution was developed on thin layer chromatography (developing solvent: chloroform/methanol/0.25% magnesium chloride aqueous solution=65/25/4 by volume) and exposed to an imaging plate to obtain a chromatogram by BAS 1000 Imaging Analyzer (manufactured by Fuji Photo Film). In this case, bands of only [1-$^{14}$C] stearic acid and a newly formed galactosyl ceramide were detected.

The portion corresponding to the galactosyl ceramide was collected from the thin layer plate and extracted with chloroform/methanol (2/1 by volume). The extract was evaporated to dryness and dissolved in 10 μl of 50 mM acetate buffer (pH 6.0) containing 16 mU β-galactosidase (derived from Jack bean) and 0.4% taurodeoxycholic acid to carry out overnight enzyme digestion at 37° C. The reaction solution was again developed on thin layer chromatography (developing solvent: chloroform/methanol/liquid ammonia=90/10/1 by volume) and analyzed by BAS 1000 Imaging Analyzer (manufactured by Fuji Photo Film) to find a band having the same Rf value of ceramide. Also, when the same reaction, thin layer chromatography and extraction steps were carried out using un-labeled stearic acid and the thus obtained product was analyzed by fast atom bombardment mass spectrometry (FAB-MS), a peak of m/z=462 which coincided with the parent ion of galactosyl ceramide and a fragment ion peak of m/z=548 which coincided with the molecular ion peak of ceramide were detected. On the basis of these results, it was revealed that the fatty acid was transferred to the amino group of the sphingosine moiety by a reverse reaction.

EXAMPLE 13

Synthesis of Shpingomyeline by SCDase

A 50 μl portion of 50 mM acetate buffer (pH 6.0) containing 50 nmol sphingosylphosphorylcholine (lysosphingomyelin, manufactured by Sigma), 5 nmol [1-$^{14}$C] stearic acid, 0.8% Triton X-100 and 150 μU SCDase derived from the genus Pseudomonas was allowed to react overnight at 37° C.

The reaction solution was developed on thin layer chromatography (developing solvent: chloroform/methanol/0.02% calcium chloride aqueous solution=5/4/1 by volume) and analyzed by BAS 1000 Imaging Analyzer (manufactured by Fuji Photo Film). In this case, bands of only [1-$^{14}$C] stearic acid and a newly formed sphingomyelin were detected.

The portion corresponding to the sphingomyelin was collected from the thin layer plate, extracted and then evaporated to dryness to obtain a reverse reaction product. The product was dissolved in 20 μl of 25 mM phosphate buffer (pH 7.5) containing 35.7 μU sphingomyelinase derived from Staphylococcus aureus (manufactured by Sigma) to carry out overnight enzyme digestion at 37° C.

The reaction solution was again developed on thin layer chromatography (developing solvent: chloroform/methanol/liquid ammonia=90/10/1 by volume) and analyzed by BAS 1000 Imaging Analyzer to find a band having the same Rf value of ceramide. On the basis of these results, it was revealed that the fatty acid was transferred to the amino group of the sphingosine moiety by a reverse reaction.

EXAMPLE 14

Reverse Reaction on Various Acceptors by SCDase-1

A 10 μl portion of 50 mM acetate buffer (pH 6.0) containing 1 nmol [1-$^{14}$C] stearic acid, 1 nmol lysosphingolipid, 0.8% Triton X-100 and 30 μU SCDase derived from the genus Pseudomonas was subjected to overnight reaction at 37° C. The thus obtained reaction solution was developed on thin layer chromatography and exposed to an imaging plate to carry out for determining the reaction product by BAS 1000 Imaging Analyzer (manufactured by Fuji Photo Film). The results are shown in Table 4.

As shown in Table 4, the enzyme can act not only upon various members of lysoglycosphingolipid broadly but also upon lysosphingophospholipid and sphingosine using them as acceptors.

TABLE 4

| Lysosphingolipid | Relative activity (%) |
| --- | --- |
| Galactosylsphingosine | 100.0 |
| Lysosulfatide | 59.6 |
| Lysolactosyl ceramide | 37.2 |
| Lysoglboside | 34.1 |
| Lysoganglioside GM1a | 15.4 |
| Lysosphingomyelin | 5.7 |
| Sphingosine | 11.5 |

EXAMPLE 15

Reverse Reaction on Various Acceptors by SCDase-2

A 41.6 µl portion of 25 mM glycine-sodium hydroxide buffer (pH 11) containing 66.6 nmol N-trifluoroacetylated aminododecanoic acid, 33.3 nmol lysosphingolipid, 0.3% Triton X-100 and 148 µU SCDase derived from the genus Pseudomonas was subjected to 48 hours of reaction at 37° C.

The thus obtained reaction solution was developed on thin layer chromatography, a glycosphingolipid was colored with orcinol-sulfuric acid, and other sphingolipids with Coomassie Brilliant Blue, and then determination of the reaction product was carried out by Imaging Densitometer (manufactured by Bio-Rad). The results are shown in Table 5.

As shown in Table 5, similar to Example 14, the enzyme can act not only on various members of lysosphingolipid broadly but also on sphingosine using it as a receptor.

TABLE 5

| Lysosphingolipid | Reaction Efficiency (%) |
| --- | --- |
| Sphingosine | 69 |
| Lysoganglioside GM3 | 24 |
| Lysoganglioside GD3 | 13 |
| Lysoganglioside GM1a | 29 |
| Lysoganglioside GD1a | 32 |

EXAMPLE 16

Specificity of SCDase Reverse Reaction for Fatty Acid Molecular Types

A 50 µl portion of 50 mM acetate buffer (pH 6.0) containing 5 nmol galactosylsphingosine (manufactured by Sigma), 5 nmol various non-labeled fatty acids, 0.8% Triton X-100 and 150 µU SCDase derived from the genus Pseudomonas was allowed to react overnight at 37° C.

Figure 13:
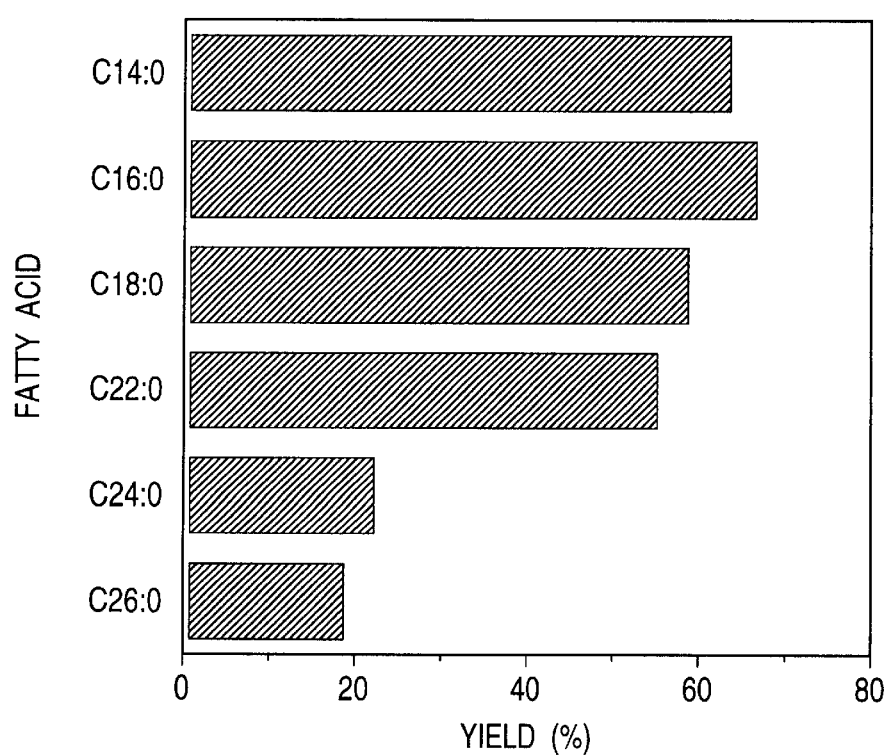
FIG. 13 is a graph which shows the specificity of a reverse reaction by an SCDase for fatty acid molecular types.

The thus obtained reaction solution was developed on thin layer chromatography, and the reaction products were colored by orcinol-sulfuric acid method and determined using Chromatoscanner CS 9000 (manufactured by Shimadzu Corporation). The results are shown in FIG. 13. That is, FIG. 13 is a graph which shows the specificity of the SCDase reverse reaction for fatty acid molecular types, in which the fatty acid is plotted as ordinate and the yield (%) as abscissa.

EXAMPLE 14

Optimum pH of Reverse Reaction by SCDase

Figure 14:
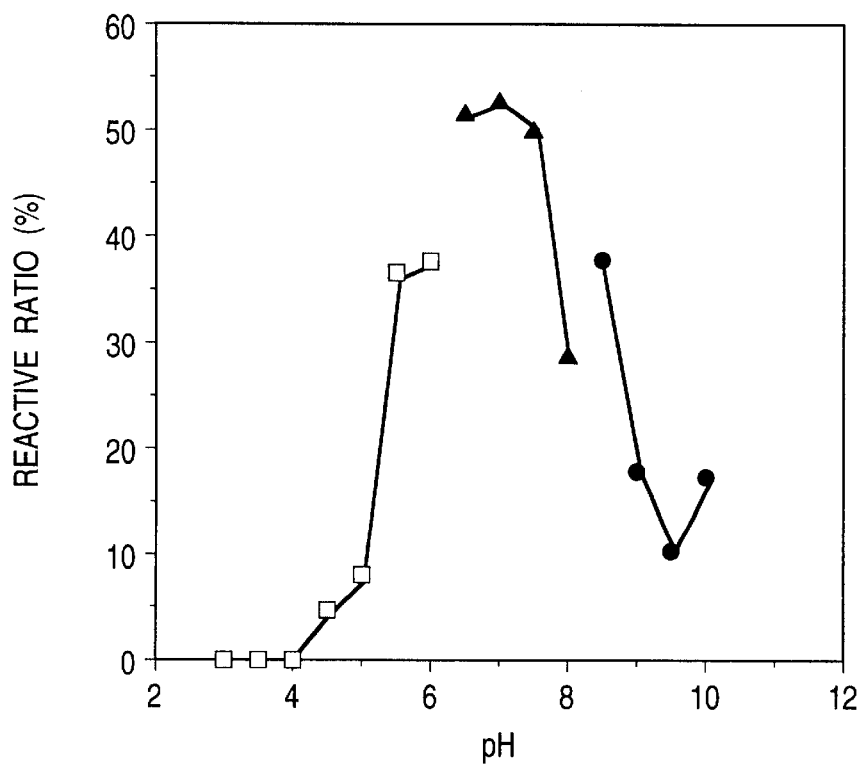
FIG. 14 is a graph which shows the optimum pH of a reverse reaction by an SCDase.

A 10 µl portion of each of various buffer solutions, each containing 1 nmol galactosylsphingosine, 1 nmol [1-$^{14}$C] stearic acid, 0.8% Triton X-100 and 30 µU SCDase derived from the genus Pseudomonas was allowed to react at 37° C. for 3 hours. The results are shown in FIG. 14. That is, FIG. 14 is a graph which shows the optimum pH of the reverse reaction, in which the reactive ratio (%) is plotted as ordinate and the pH as abscissa. In FIG. 14, □ stands for the acetate buffer, ▲ stands for the phosphate buffer and ● stands for the glycine-NaOH buffer.

EXAMPLE 18

Fatty Acid Exchange Reaction on Various Acceptors by SCDase

A 10 µl portion of 50 mM acetate buffer (pH 6.0) containing 1 nmol [1-$^{14}$C] stearic acid, 1 nmol sphingolipid, 0.8% Triton X-100 and 30 µU SCDase derived from the genus Pseudomonas was allowed to react overnight at 37° C.

The thus obtained reaction solution was developed on thin layer chromatography and exposed to an imaging plate to carry out determination of the reaction product by BAS 1000 Imaging Analyzer (manufactured by Fuji Photo Film). The results are shown in Table 6.

As shown in Table 6, the enzyme can perform fatty acid exchange reaction broadly on sphingolipids.

TABLE 6

| Sphingolipid | Relative activity (%) |
| --- | --- |
| Galactosyl ceramide | 100.0 |
| Glucosyl ceramide | 129.0 |
| Sulfatide | 31.7 |
| Lactosyl ceramide | 112.0 |
| Asialo GM1 | 164.0 |
| Globoside | 141.0 |
| Ganglioside GM3 | 54.4 |
| Ganglioside GM2 | 5.5 |
| Ganglioside GM1a | 2.4 |
| Ganglioside GD1a | 6.2 |
| Ganglioside GD1b | 1.2 |
| Sphingomyelin | 2.9 |
| Ceramide | 77.5 |

EXAMPLE 19

Examination of Reaction Conditions

In order to examine conditions for the hydrolysis reaction, the reverse reaction and the fatty acid exchange reaction, reactions were carried out under the following conditions (A) and (B). Reaction conditions (A)

A 200 µl portion of 25 mM phosphate buffer (pH 6.0) containing 120 µU SCDase derived from the genus Pseudomonas and 0.8% Triton X-100 is supplemented, as the substrate, with 100 µM $^{14}$C-galactosyl ceramide at the time of the hydrolysis reaction, 100 µM [1-$^{14}$C] stearic acid and 100 µM galactosylsphingosine at the time of the reverse reaction or 100 µM [1-$^{14}$C] stearic acid and 100 µM galactosyl ceramide at the time of the fatty acid exchange reaction.

Reaction Conditions (B)

A 200 µl portion of 25 mM phosphate buffer (pH 7.0) containing 120 µU SCDase derived from the genus Pseudomonas and 0.1% Triton X-100 is supplemented, as the substrate, with 100 µM $^{14}$C-galactosyl ceramide at the time of the hydrolysis reaction, 100 µM [1-$^{14}$C] stearic acid and 100 µM galactosylsphingosine at the time of the reverse reaction or 100 µM [1-$^{14}$C] stearic acid and 100 µM galactosyl ceramide at the time of the fatty acid exchange reaction.

Under the above conditions, each reaction was carried out at 37° C., and a 20 μl portion of the sample was collected from each reaction solution after 0.25, 0.5, 1, 3, 7 or 21 hours of the reaction and heated at 100° C. for 5 minutes to stop the reaction.

Figure 15:
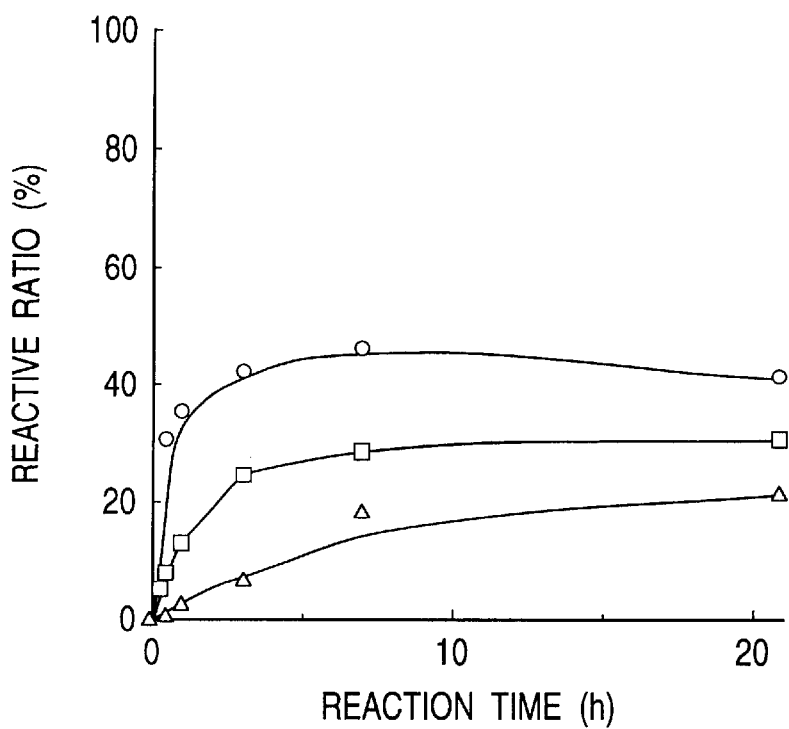
FIGS. 15(A) and 15(B) are a graph which shows the reaction ratios of a hydrolysis reaction, a reverse reaction and a fatty acid exchange reaction by an SCDase.
Figure 15:
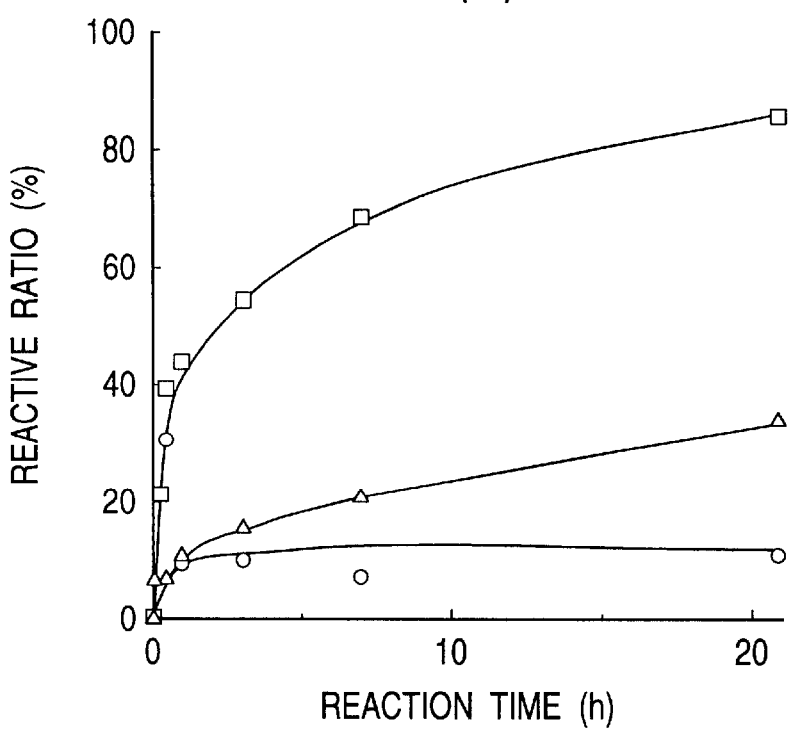

Each of the thus obtained reaction solutions was developed on thin layer chromatography (developing solvent: chloroform/methanol/0.02% calcium chloride aqueous solution=5/4/1 by volume), and the reaction product and unreacted substance were determined by BAS 1000 Imaging Analyzer (manufactured by Fuji Photo Film) to calculate the reaction efficiency. The results are shown in FIG. 15. That is, FIG. 15 is a graph which shows the reaction efficiencies of the hydrolysis reaction, the reverse reaction and the fatty acid exchange reaction by the SCDase under the above-described reaction conditions (A) and (B), in which the reaction ratio (%) is plotted as ordinate and the reaction time (h) as abscissa. In FIG. 15, ○ stands for the hydrolysis reaction, □ stands for the reverse reaction and Δ stands for the fatty acid exchange reaction, each as its reaction ratio.

As the results, it was revealed that the hydrolysis reaction of the SCDase preferentially progresses when the reaction solution has an acidic pH and contains a surfactant in a high concentration, and each of the reverse reaction and fatty acid exchange reaction of the SCDase preferentially progresses when the reaction solution is neutral and when concentration of the surfactant is reduced.

EXAMPLE 20

Synthesis of $^{14}$C Ceramide

A 100 nmol (5.0 μCi) portion of [1-$^{14}$C] palmitic acid (manufactured by Amersham) and 200 nmol of sphingosine dissolved in ethanol were put into a reaction vessel and completely dried with nitrogen gas. A 0.5 ml portion of 50 mM phosphate buffer (pH 7.0) containing 0.6% Triton X-100 was added to the vessel, thoroughly stirred and then homogenized by ultrasonic treatment. The thus homogenized solution was mixed with 0.5 ml SCDase derived from the genus Pseudomonas (1 mU/ml) and was allowed to react at 37° C. for 20 hours.

After completion of the reaction, the thus obtained reaction solution was dried using a centrifugation evaporator, the thus dried reaction product was dissolved in 1 ml of hexane/ether/acetic acid (50/50/1 by volume) and applied to Sep-Pak® Silica Cartridge which had been equilibrated with the same solution, unreacted [1-$^{14}$C] palmitic acid was washed out with 10 ml of the same solution and then $^{14}$C ceramide was eluted with 10 ml of chloroform/methanol (2/1 by volume).

The eluate was dried with nitrogen gas, suspended in distilled water and then homogenized by ultrasonic treatment. The thus homogenized solution was applied to Sep-Pak® C18 Cartridge. The cartridge was washed with 20 ml of distilled water, and $^{14}$C ceramide was eluted with 3 ml of methanol and 10 ml of chloroform/methanol (2/1 by volume).

Next, the thus obtained eluate was dried with nitrogen gas, dissolved in chloroform/methanol/distilled water (90/10/1 by volume) and then applied to Sep-Pak® CM Cartridge which had been equilibrated with the same solution for adsorbing unreacted sphingosines. In this case, the passed fraction was dried with nitrogen gas to obtain 66 nmol (3.3 μCi) purified $^{14}$C ceramide containing fatty acids and sphingosines at 1% or less.

EXAMPLE 21

Synthesis of Aminoceramide and its Fluorescent Derivative

A 41.6 ml portion of 25 mM glycine-sodium hydroxide buffer (pH 11) containing 66.6 μmol N-trifluoroacetylated aminododecanoic acid, 33.3 μmol sphingosine (manufactured by Sigma), 0.3% Triton X-100 and 148 mU Pseudomonas SCDase was allowed to react at 37° C. for 48 hours.

After completion of the reaction, the reaction solution was applied to C18 reverse phase silica gel column, the column was washed with water for desalting and then N-trifluoroacetylated aminoceramide was eluted with chloroform/methanol (2/1 by volume). After evaporation of the solvent, the resulting residue was dissolved in chloroform/methanol/water (90/10/1 by volume) and applied to Sep-Pak® CM Cartridge (manufactured by Waters) for adsorbing unreacted sphingosines and to obtain an unadsorbed fraction containing N-trifluoroacetylated aminoceramide. The unadsorbed fraction was applied to Sep-Pak® QMA Cartridge (manufactured by Waters) for adsorbing unreacted N-trifluoroacetylated aminododecanoic acid and to obtain an unadsorbed fraction containing N-trifluoroacetylated aminoceramide.

A 20 ml portion of chloroform/methanol (2/1 by volume) containing the thus obtained N-trifluoroacetylated aminoceramide and 1% sodium methoxide was allowed to react overnight at room temperature. After completion of the reaction, the solvent was evaporated, the resulting residue was suspended in water and applied to Sep-Pak® C18 Cartridge (manufactured by Waters), the column was washed with water to effect desalting and then aminoceramide was eluted with chloroform/methanol (2/1 by volume). After evaporation of the solvent, the resulting residue was dissolved in chloroform/methanol/water (60/30/5 by volume), applied to Sep-Pak® CM Cartridge and eluted with chloroform/methanol/1 N HCl (60/30/5 by volume), and then the eluent was dried to obtain 5.6 μmol of purified aminoceramide.

A 70 μl portion of 100 nmol aminoceramide dissolved in methanol, 20 μl of 50 mM NBD fluoride (manufactured by Sigma) ethanol solution and 10 μl of triethylamine were allowed to undergo 1 hour of reaction at 60° C. After completion of the reaction, the solvent was evaporated, the resulting residue was dissolved in hexane/ether/acetic acid (50/50/1 by volume) and applied to Sep-Pak® Silica Cartridge (manufactured by Waters) and eluted with chloroform/methanol (2/1 by volume), and then the eluate was dried to obtain 30 nmol of purified NBD ceramide.

EXAMPLE 22

Screening of Limulus Polyphemus Ceramidase Using Fluorescent Sphingolipid Derivative NBD Ceramide A 10 μl of serum obtained by centrifugation of Limulus polyphemus blood was allowed to undergo 18 hours of reaction at 37° C. with 10 μl of 50 mM acetate buffer (pH 5.0) containing 1 nmol of NBD ceramide prepared in Example 21 and 0.5% Triton X-100. After completion of the reaction, the reaction solution was developed on thin layer chromatography (developing solvent: chloroform/methanol/25% liquid ammonia=90/20/0.5 by volume) and detected under an ultraviolet ray lamp. In this case, a newly formed NBD aminododecanoic acid was detected, so that a ceramidase activity was detected in the Limulus polyphemus serum.

In order to confirm that the ceramidase activity found in the Limulus polyphemus serum is really a ceramidase-derived activity, the ceramidase was purified to find that it was an acidic ceramidase having an optimum pH of 4.5 and a molecular weight of about 205 kDa when measured by a gel filtration method. It was found also that this Limulus polyphemus ceramidase hydrolyzes N-stearoylsphingosine (C18:0, d18:1) most efficiently and has activity also on a ceramide containing sphinganine or phytosphingosine as the long-chain base.

Thus, the presence of an invertebrate ceramidase which had not been known was revealed for the first time by the use of the fluorescent sphingolipid derivative NBD ceramide obtained by the production method of the present invention, and it was confirmed that the fluorescent sphingolipid derivative NBD ceramide is useful as a substrate for use in the measurement of ceramidase activity.

EXAMPLE 23

Measurement of Ceramidase Activity in B16 Cells Using Radioisotope Labeled $^{14}$C Ceramide (C12-$^{14}$C-Cer) and Fluorescent Sphingolipid Derivative NBD Ceramide (C12-NBD-Cer) as the Substrate A cell suspension was prepared by suspending $6 \times 10^6$ of B16 cells in 200 µl of 10 mM phosphate buffer. The amount of the protein was determined using MicroBCA™ protein assay reagent (manufactured by Pierce).

Reaction Conditions 1

Under acidic condition in 10 µl of 50 mM acetate buffer (pH 4.0) containing 10 µl of the cell suspension (diluted to a protein content of 50 µg), 200 pmol of C12-NBD-Cer obtained in Example 21 or 100 pmol of C12-$^{14}$C-Cer obtained using lauric acid instead of palmitic acid used in Example 20, as the substrate, and 0.5% Triton X-100.

Reaction Conditions 2

Under neutral conditions in 10 µl of 50 mM phosphate buffer (pH 7.0) containing 10 µl of the cell suspension (diluted to a protein content of 50 µg), 200 pmol of C12-NBD-Cer or 100 pmol of C12-$^{14}$C-Cer as the substrate and 0.5% Triton X-100.

Reaction Conditions 3

Under basic condition in 10 µl of 50 mM Tris-HCl buffer (pH 8.5) containing 10 µl of the cell suspension (diluted to a protein content of 50 µg), 200 pmol C12-NBD-Cer or 100 pmol C12-$^{14}$C-Cer as the substrate and 0.5% Triton X-100.

Under each of the above conditions, the reaction was carried out at 37° C. for 3 or 6 hours. Thereafter, the reaction was stopped by adding 100 µl of chloroform/methanol (2/1 by volume) to the reaction solution. The thus obtained reaction solution was dried and then dissolved in chloroform/methanol (2/1 by volume) to be used as a sample.

Figure 16:
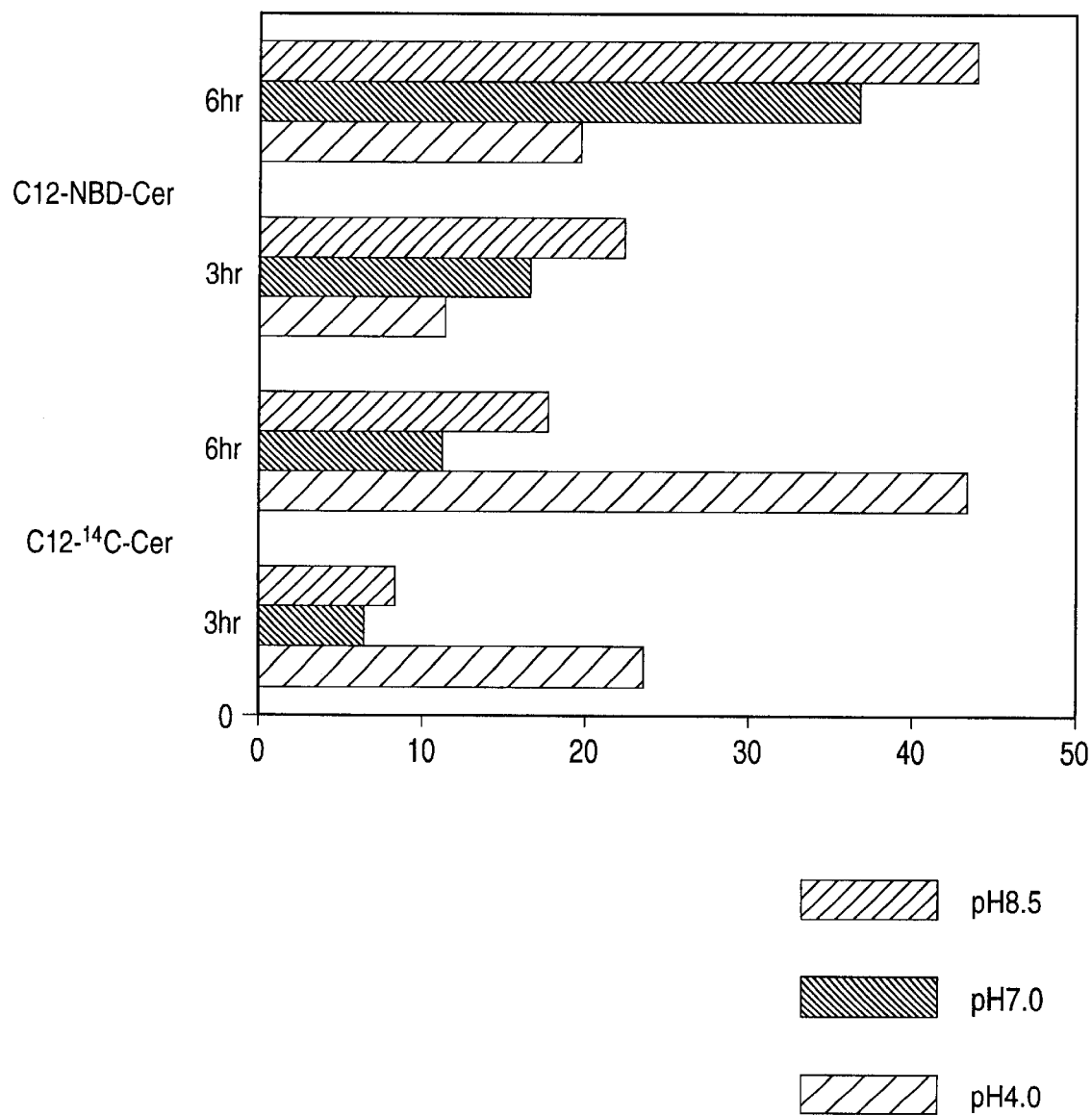
FIG. 16 is a graph which compares ceramidase activities in B16 cells.

Each of the samples was developed on thin layer chromatography (developing solvent, chloroform/methanol/25% liquid ammonia=90/20/0.5 by volume), and the released $^{14}$C fatty acid was determined using BAS 1000 Imaging Analyzer (manufactured by Fuji Photo Film) to calculate the reaction ratio. Also, the released NBD fatty acid was determined using Chromatoscanner CS 9000 (manufactured by Shimadzu Corporation), and the reaction ratio was calculated. The results are shown in FIG. 16. That is, FIG. 16 is a graph which shows comparison of the measurement of ceramidase activities in B16 cells, in which reactions of 3 hours (3 hr) and 6 hours (6 hr) using C12-NBD-Cer as the substrate and reactions of 3 hours and 6 hours using C12-$^{14}$C-Cer as the substrate are plotted in that downward order as ordinate and the decomposition ratio (%) as abscissa.

On the basis of these results, it was suggested that there are an alkaline ceramidase which acts well on C12-NBD-Cer but hardly on C12-$^{14}$C-Cer and an acidic ceramidase which acts well on C12-$^{14}$C-Cer but hardly on C12-NBD-Cer.

While the invention has been described in detail and with reference to specific examples thereof, it will be apparent to one skilled in the art that various changes and modifications can be made therein without departing from the spirit and scope thereof.

This application is based on application Nos. Hei 6-190133, 8-214065, 8-214065 and 10-96989 filed in Japan and International application No. PCT/JP97/02483, the entire contents of which are incorporated hereinto by reference.

---

What is claimed is:

1. An isolated sphingolipid ceramide N-deacylase having physicochemical properties of:
   (1) acting on a ceramide moiety in the molecule of a sphingolipid and forming a lysosphingolipid and a fatty acid,
   (2) acting on neutral glycosphingolipids, acidic glycosphingolipids, and sphingomyelins,
   (3) having a molecular weight of about 52 kDa as determined by SDS-PAGE, and
   (4) having an optimum temperature of about 40° C., obtainable from a strain belonging to Pseudomonas species.

2. The sphingolipid ceramide N-deacylase according to claim 1, wherein the strain is Pseudomonas sp. TK-4 (Deposit No. FERM BP-5096) or a mutant thereof.

3. An isolated sphingolipid ceramide N-deacylase having physicochemical properties of:
   (1) acting on a ceramide moiety in the molecule of a sphingolipid and forming a lysosphingolipid and a fatty acid,
   (2) acting on neutral glycosphingolipids, acidic glycosphingolipids, and sphingomyelins,
   (3) having an optimum pH value range of from 5 to 8.5, and
   (4) having an optimum temperature of about 40° C., obtainable from a strain belonging to Shewanella species.

4. The sphingolipid ceramide N-deacylase according to claim 3, wherein the strain is *Shewanella alga* NS-589 (Deposit No. FERM P-15700) or a mutant thereof.

5. A method for producing a sphingolipid ceramide N-deacylase which comprises:
   culturing a strain belonging to the genus Pseudomonas which is capable of producing the sphingolipid ceramide N-deacylase of claim 1 to produce the sphingolipid ceramide N-deacylase, and
   recovering the sphingolipid ceramide N-deacylase from the culture.

6. The method according to claim 5, wherein the strain is Pseudomonas sp. TK-4 (Deposit No. FERM BP-5096) or a mutant thereof.

7. A method for producing a sphingolipid ceramide N-deacylase which comprises:
   culturing a strain belonging to the genus Shewanella which is capable of producing the sphingolipid ceramide N-deacylase of claim 3 to produce the sphingolipid ceramide N-deacylase, and
   recovering the sphingolipid ceramide N-deacylase from the culture.

8. The method according to claim 7, wherein the strain is *Shewanella alga* NS-589 (Deposit No. FERM P-15700) or a mutant thereof.

9. A biologically pure culture of a bacterium belonging to the genus Pseudomonas which is capable of producing a sphingolipid ceramide N-deacylase having physiochemical properties of:
   (1) acting on a ceramide moiety in the molecule of a sphingolipid and forming a lysosphingolipid and a fatty acid,
   (2) acting on neutral glycosphingolipids, acidic glycosphingolipids, and sphingomyelins,
   (3) having a molecular weight of about 52 kDa as determined by SDS-PAGE, and
   (4) having an optimum temperature of about 40° C.

10. The bacterium according to claim 9, which is Pseudomonas sp. TK-4 (Deposit No. FERM BP-5096) or a mutant thereof.

11. A biologically pure culture of a bacterium belonging to the genus Shewanella which is capable of producing a sphingolipid ceramide N-deacylase having physiochemical properties of:
    (1) acting on a ceramide moiety in the molecule of a sphingolipid and forming a lysosphingolipid and a fatty acid,
    (2) acting on neutral glycosphingolipids, acidic glycosphingolipids, and sphingomyelins,
    (3) having an optimum pH value range of from 5 to 8.5, and
    (4) having an optimum temperature of about 40° C.

12. The bacterium according to claim 11, which is *Shewanella alga* NS-589 (Deposit No. FERM P-15700) or a mutant thereof.

* * * * *

SEQUENCE LISTING

<160> NUMBER OF SEQ ID NOS: 12

<210> SEQ ID NO 1
<211> LENGTH: 439
<212> TYPE: PRT
<213> ORGANISM: Unknown
<220> FEATURE:
<223> OTHER INFORMATION: Description of Unknown Organism: sphingolipid
      ceramide N-deacylase

<400> SEQUENCE: 1

Glu Leu Gly Asp Tyr Gly Ala Trp Lys Thr Leu Leu Asn Leu Thr Ser
 1               5                  10                  15

Pro Pro Lys Ala Asp Asn Pro Val Arg Ala Glu Gln Arg Val Gly Pro
            20                  25                  30

Tyr Pro Met Leu Ala Asn Pro Ala Gly Phe Arg Ser Gly Phe Thr Pro
        35                  40                  45

Thr Ala Tyr Phe Ala Trp Gln Thr Val Gln Leu Ala Pro Glu Thr Gly
    50                  55                  60

Ala Val Cys Gly Asp Gly Ser Pro Tyr Lys Phe Phe Val Asn Arg Met
65                  70                  75                  80

Pro Asn Thr Ser Asn Thr Leu Ile Tyr Met Glu Gly Gly Ala Cys
            85                  90                  95

Trp Asp Tyr Ala Ser Cys Ser Gly Gln Ala Gly Ile Arg Gly Ala Arg
                100                 105                 110

Asn Pro Asn Gly Ile Pro Asp Asp Tyr Met Lys Leu Ala Asn Pro Gln
            115                 120                 125

Ala Ser Leu Val Ser Pro Phe Val Arg Leu His Pro Tyr Ser Arg
130                 135                 140

Val Lys Thr Gln Gly Trp Asn Ile Val Tyr Ile Pro Tyr Cys Thr Gly
145                 150                 155                 160

Asp Leu Tyr Ala Gly Asp Lys Val Ala Val Tyr Asp Asp Pro Ser Gly
                165                 170                 175

Lys Lys Pro Pro Leu Val Trp His His Asn Gly Leu Arg Asn Gly Arg
            180                 185                 190

Ala Val Leu Gly Trp Leu Lys Asp Asn Leu Glu Arg Pro Gly Gln Met
            195                 200                 205

Leu Ser Thr Gly Cys Ser Ala Gly Ala Gly Ser Leu Ile Ser His
    210                 215                 220

Ser Val Leu Arg Gln Asp Leu Ala Pro Asp Arg Gly Phe Leu Ile Asp
225                 230                 235                 240

Asp Ser Gly Pro Val Phe Ser Ala Ala Val Gly Gly Asp Ser Gln Thr
                245                 250                 255

Tyr Pro Ser Leu Pro Leu Gln Asn Leu Ile Arg Ser Ala Trp Gly Leu
            260                 265                 270

Asp Gln Gly Pro Leu Gln Phe Leu Gln Ser Arg Leu Pro Gly Val Ser
            275                 280                 285

Leu Ser Asn Leu Gly Ser Leu Tyr Pro Ala Leu Ala Ala Asn Phe Pro
    290                 295                 300

Gly Asp Arg Leu Gly His Thr His Phe Trp Gln Asp Leu Asn Tyr Ser
305                 310                 315                 320

Ser Tyr Ser Tyr Glu Arg Phe Tyr Pro Glu Ile Ala Asn Ala Pro Asp
                325                 330                 335

Lys Ala Thr Lys Glu Ala Leu Ile Lys Ala Lys Trp Gln Val Asp Thr
            340                 345                 350

Ala Arg Leu Arg Asp Thr Leu Ala Asn Leu Pro Asn Phe Gly Gly Tyr
            355                 360                 365

Phe Pro Gln Tyr Arg Ala Leu Asn Glu Ser His Cys Thr Thr Ile Val
370                 375                 380

Asp Phe Ala Asn Gly Asp Ile Gln Glu Gln Gly Leu Glu Leu Ser His
385                 390                 395                 400

Phe Ile Asp Asn Val Leu Asn Gly Gln Gly Pro Val Leu Asp Ala Ser
                405                 410                 415

Glu Leu Ser Asp Ser Ala Asp Arg Ala Lys Pro Asn Asn Leu Ile Tyr
            420                 425                 430

Asp Ala Ile Asn Lys Leu Leu
            435

<210> SEQ ID NO 2
<211> LENGTH: 1317
<212> TYPE: DNA
<213> ORGANISM: Unknown
<220> FEATURE:
<223> OTHER INFORMATION: Description of Unknown Organism: portion of -continued gene sequence which encodes a polypeptide having SCDase activity

<400> SEQUENCE: 2

| | | | | | |
|---|---|---|---|---|---|
| gaactcggtg | actacggtgc | ctggaagaca | cttctcaacc | tgacctctcc | gcccaaggct | 60 |
| gataacccg | tgcgggccga | gcagcgcgtt | ggccctacc | cgatgctggc | caacccggcc | 120 |
| ggattcaggt | ccggcttcac | gccgacggcc | tacttcgcct | gcagaccgt | ccagcttgca | 180 |
| ccggagaccg | gagcggtatg | cggtgacggc | tcgccctaca | agttcttcgt | caaccggatg | 240 |
| ccgaacacca | gcaacaccct | gatctacatg | gaaggcggcg | gcgcctgctg | ggactacgcc | 300 |
| agctgttccg | gccaggccgg | catccgcggc | gcgcgcaacc | ccaatggcat | tccggatgac | 360 |
| tacatgaagc | tggcgaaccc | ccaagccagt | ctggtcagcc | ccttcgtcgt | gcgcctccac | 420 |
| ccgtactccc | gggtgaagac | ccaaggctgg | aacatcgtct | acatcccta | ttgcaccggt | 480 |
| gacctgtatg | ccggcgacaa | ggtggcggtc | tatgacgatc | cgagcgggaa | gaagcctccc | 540 |
| ctggtctggc | atcacaacgg | cttgcgcaac | ggtcgggcag | tgctcggctg | gctgaaggac | 600 |
| aacctggagc | gccccggcca | gatgctttcc | accggctgca | gtgccggcgg | tgcgggcagc | 660 |
| ctgatcagtc | actcggtgct | tcgccaggac | ctcgcgccgg | atcgcggctt | cctgatcgac | 720 |
| gactccgggc | cggtcttcag | cgctgccgtg | ggcggcgaca | gccagaccta | cccctcgctg | 780 |
| ccgctgcaga | acctcatccg | cagcgcctgg | gggcttgacc | aggggccgct | gcagttcctg | 840 |
| cagtcgcgcc | tgccgggcgt | gagtctctcc | aacctgggca | gcctctaccc | ggccctggcg | 900 |
| gccaacttcc | cggggaccg | cctgggtcac | acgcacttct | gcaggacct | gaactactcg | 960 |
| tcctattcct | atgagcggtt | ctacccggaa | atcgccaatg | ctccggacaa | ggccaccaag | 1020 |
| gaggcgctga | tcaaggccaa | gtggcaggtg | acaccgcgc | gcctgcgcga | caccctggcc | 1080 |
| aacctgccga | acttcgggg | ctatttcccg | cagtaccggg | cccttaacga | gagccactgc | 1140 |
| accaccatcg | tcgacttcgc | caacggcgat | attcaggagc | agggtctgga | actcagccac | 1200 |
| ttcatcgaca | acgtgctcaa | tggccaaggt | ccggtgctgg | acgcctccga | gctcagcgat | 1260 |
| tcggcggacc | gagccaagcc | caacaacctg | atctacgacg | ccatcaataa | actgctc | 1317 |

<210> SEQ ID NO 3
<211> LENGTH: 15
<212> TYPE: PRT
<213> ORGANISM: Unknown
<220> FEATURE:
<223> OTHER INFORMATION: Description of Unknown Organism: N-terminal
      amino acid sequence N
<220> FEATURE:
<223> OTHER INFORMATION: Xaa is any, other or unknown

<400> SEQUENCE: 3

Gln Leu Gly Asp Tyr Gly Ala Xaa Lys Tyr Leu Leu Asn Leu Thr
 1               5                  10                  15

<210> SEQ ID NO 4
<211> LENGTH: 25
<212> TYPE: DNA
<213> ORGANISM: Unknown
<220> FEATURE:
<223> OTHER INFORMATION: Description of Unknown Organism: primer-1
<220> FEATURE:
<223> OTHER INFORMATION: n bases are A, T, C, G, other or unknown

<400> SEQUENCE: 4
gcgaattcga rttrggngay taygg                                          25

```
<210> SEQ ID NO 5
<211> LENGTH: 25
<212> TYPE: DNA
<213> ORGANISM: Unknown
<220> FEATURE:
<223> OTHER INFORMATION: Description of Unknown Organism: primer-2
<220> FEATURE:
<223> OTHER INFORMATION: n bases are A, T, C, G, other or unknown

<400> SEQUENCE: 5
gcgaattcga rttrggngay taygg                                             25

<210> SEQ ID NO 6
<211> LENGTH: 9
<212> TYPE: PRT
<213> ORGANISM: Unknown
<220> FEATURE:
<223> OTHER INFORMATION: Description of Unknown Organism: partial amino
      acid sequence N-8

<400> SEQUENCE: 6

Val Ala Val Tyr Asp Asp Pro Ser Gly
 1               5

<210> SEQ ID NO 7
<211> LENGTH: 25
<212> TYPE: DNA
<213> ORGANISM: Unknown
<220> FEATURE:
<223> OTHER INFORMATION: Description of Unknown Organism: primer-3
<220> FEATURE:
<223> OTHER INFORMATION: n bases are A, T, C, G, other or unknown

<400> SEQUENCE: 7
gcgaattcga rttrggngay taygg                                             25

<210> SEQ ID NO 8
<211> LENGTH: 9
<212> TYPE: PRT
<213> ORGANISM: Unknown
<220> FEATURE:
<223> OTHER INFORMATION: Description of Unknown Organism: partial amino
      acid sequence N-32
<220> FEATURE:
<223> OTHER INFORMATION: Xaa is any, other or unknown

<400> SEQUENCE: 8

Xaa Gln Val Asp Thr Ala Arg Leu Arg
 1               5

<210> SEQ ID NO 9
<211> LENGTH: 13
<212> TYPE: PRT
<213> ORGANISM: Unknown
<220> FEATURE:
<223> OTHER INFORMATION: Description of Unknown Organism: partial amino
      acid sequence N-34
<220> FEATURE:
<223> OTHER INFORMATION: Xaa is any, other or unknown

<400> SEQUENCE: 9

Xaa Asn Leu Glu Arg Pro Gly Gln Met Leu Ser Thr Gly
 1               5                  10

<210> SEQ ID NO 10
<211> LENGTH: 533
<212> TYPE: DNA
<213> ORGANISM: Unknown
<220> FEATURE:
```

<223> OTHER INFORMATION: Description of Unknown Organism: DNA fragment

<400> SEQUENCE: 10

| | | | | | |
|---|---|---|---|---|---|
| gaattcgaat | tgggtgacta | tggtgcctgg | aagacacttc | tcaacctgac | ctctccgccc | 60 |
| aaggctgata | accccgtgcg | ggccgagcag | cgcgttggcc | cctacccgat | gctggccaac | 120 |
| ccggccggat | tcaggtccgg | cttcacgccg | acggcctact | tcgcctggca | gaccgtccag | 180 |
| cttgcaccgg | agaccggagc | ggtatgcggt | gacggctcgc | cctacaagtt | cttcgtcaac | 240 |
| cggatgccga | acaccagcaa | caccctgatc | tacatggaag | gcggcggcgc | ctgctgggac | 300 |
| tacgccagct | gttccggcca | ggccggcatc | cgcggcgcgc | gcaaccccaa | tggcattccg | 360 |
| gatgactaca | tgaagctggc | gaaccccaa | gccagtctgg | tcagccccTT | cgtcgtgcgc | 420 |
| ctccacccgt | actcccgggt | gaagacccaa | ggctggaaca | tcgtctacat | ccctattgc | 480 |
| accggtgacc | tgtatgccgg | cgacaaggtg | gcagtgtatg | acgatccgaa | ttc | 533 |

<210> SEQ ID NO 11
<211> LENGTH: 1392
<212> TYPE: DNA
<213> ORGANISM: Unknown
<220> FEATURE:
<223> OTHER INFORMATION: Description of Unknown Organism: ORF of SCDase

<400> SEQUENCE: 11

| | | | | | |
|---|---|---|---|---|---|
| atgaggctcg | ctacgcgcct | gcgctgcagc | atcatcttgt | tgtcctgcct | gttgccaacc | 60 |
| ttccaagccc | acgccgaact | cggtgactac | ggtgcctgga | agacacttct | caacctgacc | 120 |
| tctccgccca | aggctgataa | ccccgtgcgg | gccgagcagc | gcgttggccc | ctacccgatg | 180 |
| ctggccaacc | cggccggatt | caggtccggc | ttcacgccga | cggcctactt | cgcctggcag | 240 |
| accgtccagc | ttgcaccgga | gaccggagcg | gtatgcggtg | acggctcgcc | ctacaagttc | 300 |
| ttcgtcaacc | ggatgccgaa | caccagcaac | accctgatct | acatggaagg | cggcggcgcc | 360 |
| tgctgggact | acgccagctg | ttccggccag | gccggcatcc | gcggcgcgcg | caaccccaat | 420 |
| ggcattccgg | atgactacat | gaagctggcg | aaccccaag | ccagtctggt | cagccccttc | 480 |
| gtcgtgcgcc | tccacccgta | ctcccgggtg | aagacccaag | gctggaacat | cgtctacatc | 540 |
| ccctattgca | ccggtgacct | gtatgccggc | gacaaggtgg | cggtctatga | cgatccgagc | 600 |
| gggaagaagc | ctcccctggt | ctggcatcac | aacggcttgc | gcaacggtcg | gcagtgctc | 660 |
| ggctggctga | aggacaacct | ggagcgcccc | ggccagatgc | tttccaccgg | ctgcagtgcc | 720 |
| ggcggtgcgg | gcagcctgat | cagtcactcg | gtgcttcgcc | aggacctcgc | gccggatcgc | 780 |
| ggcttcctga | tcgacgactc | cgggccggtc | ttcagcgctg | ccgtgggcgg | cgacagccag | 840 |
| acctaccct | cgctgccgct | gcagaacctc | atccgcagcg | cctgggggct | tgaccagggg | 900 |
| ccgctgcagt | tcctgcagtc | gcgcctgccg | ggcgtgagtc | tctccaacct | gggcagcctc | 960 |
| tacccggccc | tggcggccaa | cttcccgggg | gaccgcctgg | gtcacacgca | cttctggcag | 1020 |
| gacctgaact | actcgtccta | ttcctatgag | cggttctacc | cggaaatcgc | caatgctccg | 1080 |
| gacaaggcca | ccaaggaggc | gctgatcaag | gccagtggcc | aggtggacac | cgcgcgcctg | 1140 |
| cgcgacaccc | tggccaacct | gccgaacttc | gggggctatt | tccgcagta | ccgggccctt | 1200 |
| aacgagagcc | actgcaccac | catcgtcgac | ttcgccaacg | gcgatattca | ggagcagggt | 1260 |
| ctggaactca | gccacttcat | cgacaacgtg | ctcaatggcc | aaggtccggt | gctggacgcc | 1320 |
| tccgagctca | gcgattcggc | ggaccgagcc | aagcccaaca | acctgatcta | cgacgccatc | 1380 |
| aataaactgc | tc | | | | | 1392 |

<210> SEQ ID NO 12
<211> LENGTH: 464
<212> TYPE: PRT
<213> ORGANISM: Unknown
<220> FEATURE:
<223> OTHER INFORMATION: Description of Unknown Organism: amino acid
      sequence encoded by SCDase ORF

<400> SEQUENCE: 12

Met Arg Leu Ala Thr Arg Leu Arg Cys Ser Ile Ile Leu Leu Ser Cys
 1               5                  10                  15

Leu Leu Pro Thr Phe Gln Ala His Ala Glu Leu Gly Asp Tyr Gly Ala
            20                  25                  30

Trp Lys Thr Leu Leu Asn Leu Thr Ser Pro Pro Lys Ala Asp Asn Pro
        35                  40                  45

Val Arg Ala Glu Gln Arg Val Gly Pro Tyr Pro Met Leu Ala Asn Pro
 50                  55                  60

Ala Gly Phe Arg Ser Gly Phe Thr Pro Thr Ala Tyr Phe Ala Trp Gln
 65                  70                  75                  80

Thr Val Gln Leu Ala Pro Glu Thr Gly Ala Val Cys Gly Asp Gly Ser
                85                  90                  95

Pro Tyr Lys Phe Phe Val Asn Arg Met Pro Asn Thr Ser Asn Thr Leu
            100                 105                 110

Ile Tyr Met Glu Gly Gly Gly Ala Cys Trp Asp Tyr Ala Ser Cys Ser
        115                 120                 125

Gly Gln Ala Gly Ile Arg Gly Ala Arg Asn Pro Asn Gly Ile Pro Asp
130                 135                 140

Asp Tyr Met Lys Leu Ala Asn Pro Gln Ala Ser Leu Val Ser Pro Phe
145                 150                 155                 160

Val Val Arg Leu His Pro Tyr Ser Arg Val Lys Thr Gln Gly Trp Asn
                165                 170                 175

Ile Val Tyr Ile Pro Tyr Cys Thr Gly Asp Leu Tyr Ala Gly Asp Lys
            180                 185                 190

Val Ala Val Tyr Asp Asp Pro Ser Gly Lys Lys Pro Pro Leu Val Trp
        195                 200                 205

His His Asn Gly Leu Arg Asn Gly Arg Ala Val Leu Gly Trp Leu Lys
210                 215                 220

Asp Asn Leu Glu Arg Pro Gly Gln Met Leu Ser Thr Gly Cys Ser Ala
225                 230                 235                 240

Gly Gly Ala Gly Ser Leu Ile Ser His Ser Val Leu Arg Gln Asp Leu
                245                 250                 255

Ala Pro Asp Arg Gly Phe Leu Ile Asp Asp Ser Gly Pro Val Phe Ser
            260                 265                 270

Ala Ala Val Gly Gly Asp Ser Gln Thr Tyr Pro Ser Leu Pro Leu Gln
        275                 280                 285

Asn Leu Ile Arg Ser Ala Trp Gly Leu Asp Gln Gly Pro Leu Gln Phe
    290                 295                 300

Leu Gln Ser Arg Leu Pro Gly Val Ser Leu Ser Asn Leu Gly Ser Leu
305                 310                 315                 320

Tyr Pro Ala Leu Ala Ala Asn Phe Pro Gly Asp Arg Leu Gly His Thr
                325                 330                 335

His Phe Trp Gln Asp Leu Asn Tyr Ser Ser Tyr Ser Tyr Glu Arg Phe
            340                 345                 350

Tyr Pro Glu Ile Ala Asn Ala Pro Asp Lys Ala Thr Lys Glu Ala Leu

-continued

```
                    355                 360                 365
Ile Lys Ala Lys Trp Gln Val Asp Thr Ala Arg Leu Arg Asp Thr Leu
    370                 375                 380

Ala Asn Leu Pro Asn Phe Gly Gly Tyr Phe Pro Gln Tyr Arg Ala Leu
385                 390                 395                 400

Asn Glu Ser His Cys Thr Thr Ile Val Asp Phe Ala Asn Gly Asp Ile
                405                 410                 415

Gln Glu Gln Gly Leu Glu Leu Ser His Phe Ile Asp Asn Val Leu Asn
                420                 425                 430

Gly Gln Gly Pro Val Leu Asp Ala Ser Glu Leu Ser Asp Ser Ala Asp
                435                 440                 445

Arg Ala Lys Pro Asn Asn Leu Ile Tyr Asp Ala Ile Asn Lys Leu Leu
450                 455                 460
```